US011353467B2

(12) United States Patent
Louie et al.

(10) Patent No.: US 11,353,467 B2
(45) Date of Patent: Jun. 7, 2022

(54) USE OF LIPID PARTICLES IN MEDICAL DIAGNOSTICS

(71) Applicant: The Regents of the University of California, Oakland, CA (US)

(72) Inventors: Katherine B. Louie, Walnut Creek, CA (US); Benjamin P. Bowen, Walnut Creek, CA (US); Trent R. Northen, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 868 days.

(21) Appl. No.: 14/761,587

(22) PCT Filed: Jan. 23, 2014

(86) PCT No.: PCT/US2014/012790
§ 371 (c)(1),
(2) Date: Jul. 16, 2015

(87) PCT Pub. No.: WO2014/116856
PCT Pub. Date: Jul. 31, 2014

(65) Prior Publication Data
US 2016/0003855 A1 Jan. 7, 2016
US 2017/0030935 A9 Feb. 2, 2017

Related U.S. Application Data

(60) Provisional application No. 61/756,401, filed on Jan. 24, 2013.

(51) Int. Cl.
*G01N 33/92* (2006.01)
*G01N 33/574* (2006.01)

(52) U.S. Cl.
CPC .......... *G01N 33/92* (2013.01); *G01N 33/574* (2013.01); *G01N 2405/04* (2013.01); *G01N 2405/08* (2013.01); *G01N 2458/15* (2013.01); *G01N 2560/00* (2013.01); *G01N 2800/7028* (2013.01)

(58) Field of Classification Search
None
See application file for complete search history.

(56) References Cited

U.S. PATENT DOCUMENTS 8,005,623 B2    8/2011 Hellerstein et al.
2014/0329274 A1* 11/2014 Bowen ................ G01N 33/58
                                                 435/34

FOREIGN PATENT DOCUMENTS

WO    WO 2011/163332 A2    12/2011
WO    WO 2012/170715 A1    12/2012
WO    WO 2013/003384 A1     1/2013

OTHER PUBLICATIONS

Watson, A.D Journal of Lipid Research (2006), 47(10), 2101-2111.*
Han, X. Frontiers in Bioscience (2007), 12, 2601-2615.*
Li, M. Anal Bioanal Chem (2011) 399:243-249.*
Igai, A. Cancers 2011, 3, 2462-2477.*
Woo et al. Nature Protocols, 3(8), 1341-1349,2008.*
Northern et al. Nature, 449, 1033-1037, 2007.*
Ishikawa et al. PLoS One 7(11): e48873, pp. 1-8.*
Satouchi et al. Cancer Research, 44, 1460-1464, 1984.*
Iorio et al. Cancer Res; 70(5); 2126-2135, 2010.*
Sarvaiya et al., "Proteome profile of the MCF7 cancer cell line: a mass spectrometric evaluation", Rapid Communications in Mass Spectrometry, Sep. 20, 20016, vol. 20, pp. 3039-3055.
International Search Report and Written Opinion dated Apr. 14, 2014 for International patent application PCT/US2014/012790 filed Jan. 23, 2014.
Haraszti et al., "High-resolution proteomicand lipidomic analysis of exosomes and microvesicles from different cell sources," Journal of Extracellular Vesicles 2016, 5(32570), in 14 pages.

* cited by examiner

*Primary Examiner* — Michael L Borin
(74) *Attorney, Agent, or Firm* — Sheppard, Mullin, Richter & Hampton LLP

(57) ABSTRACT

Disclosed herein are methods for identifying one or more diseased cells in a subject. Some embodiments include providing a biological sample derived from a subject, analyzing the biological sample by mass spectrometry, and determining the abundance of one or more lipids in the biological sample, wherein an altered abundance of the one or more lipids in the biological sample, as compared to a reference level, indicates a presence of one or more diseased cells in the subject from which the biological sample is derived.

10 Claims, 19 Drawing Sheets

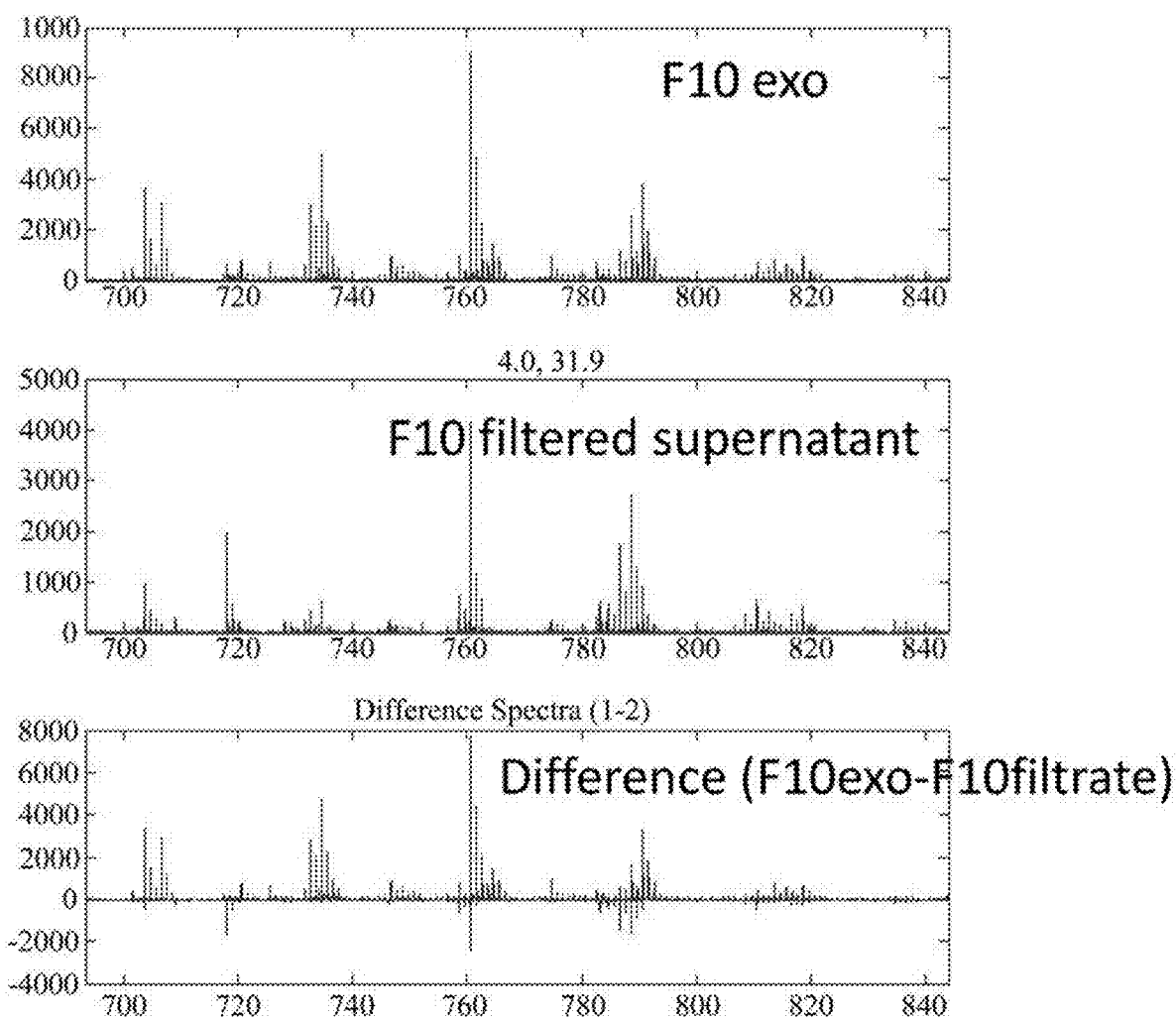

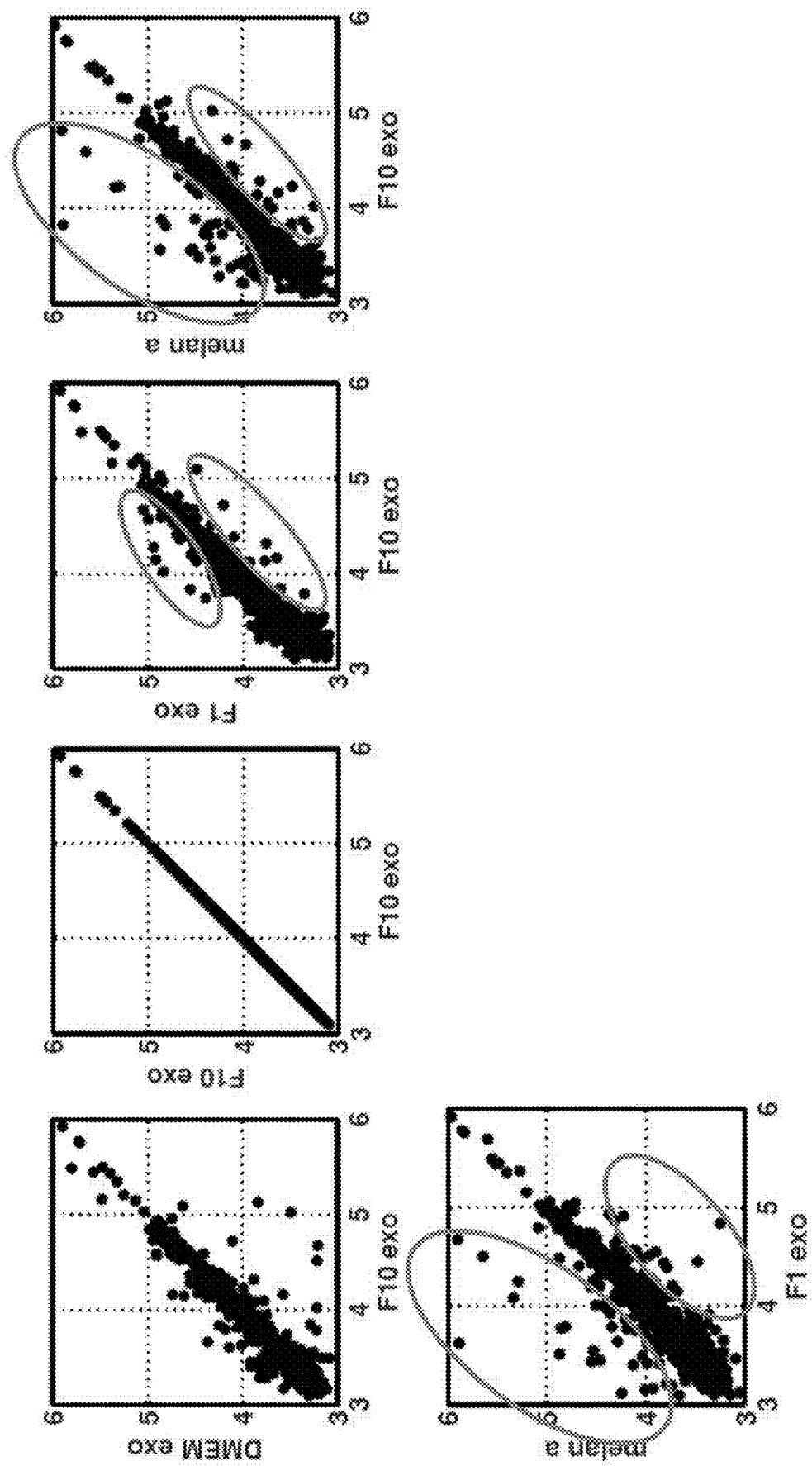

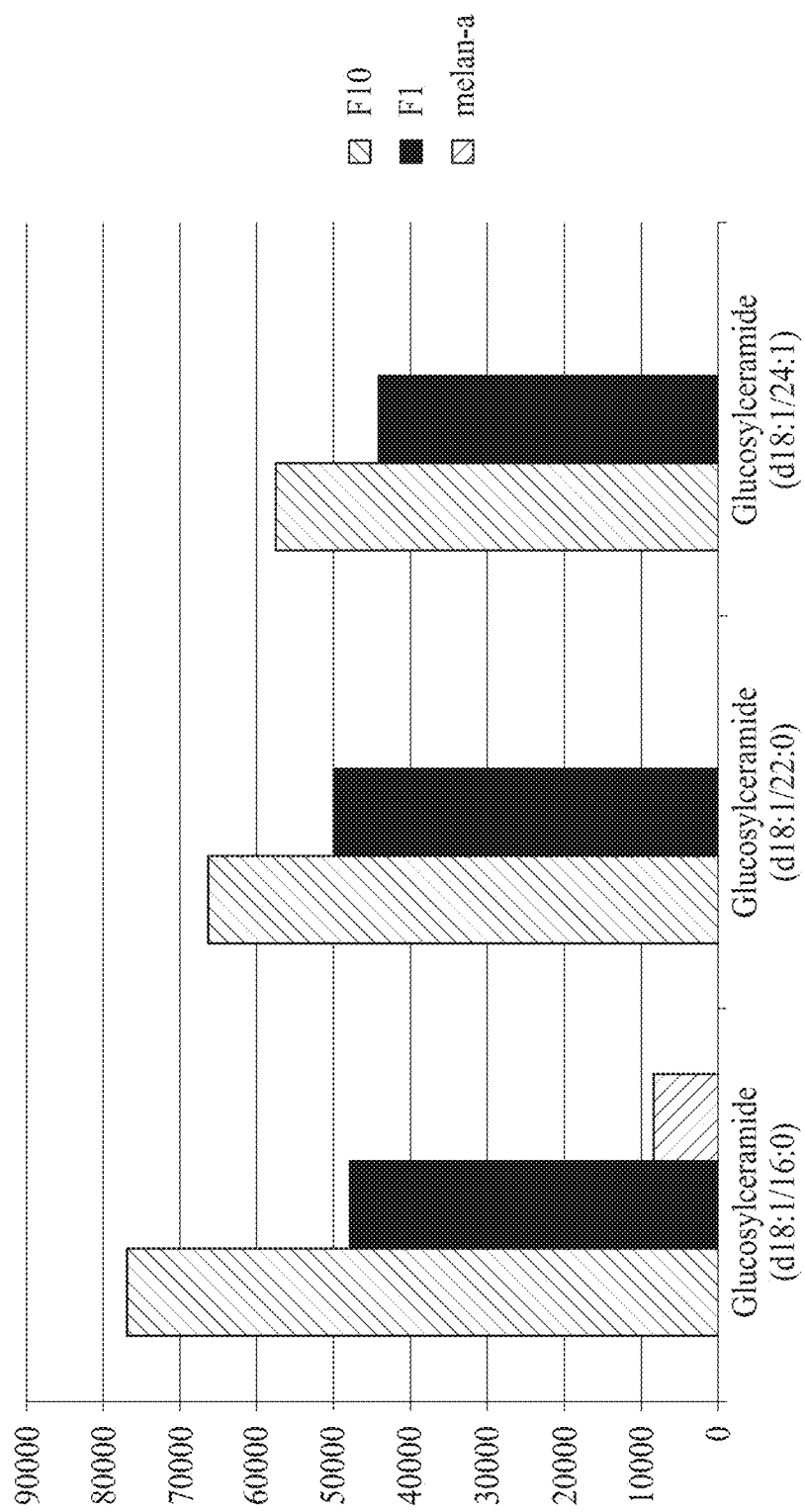

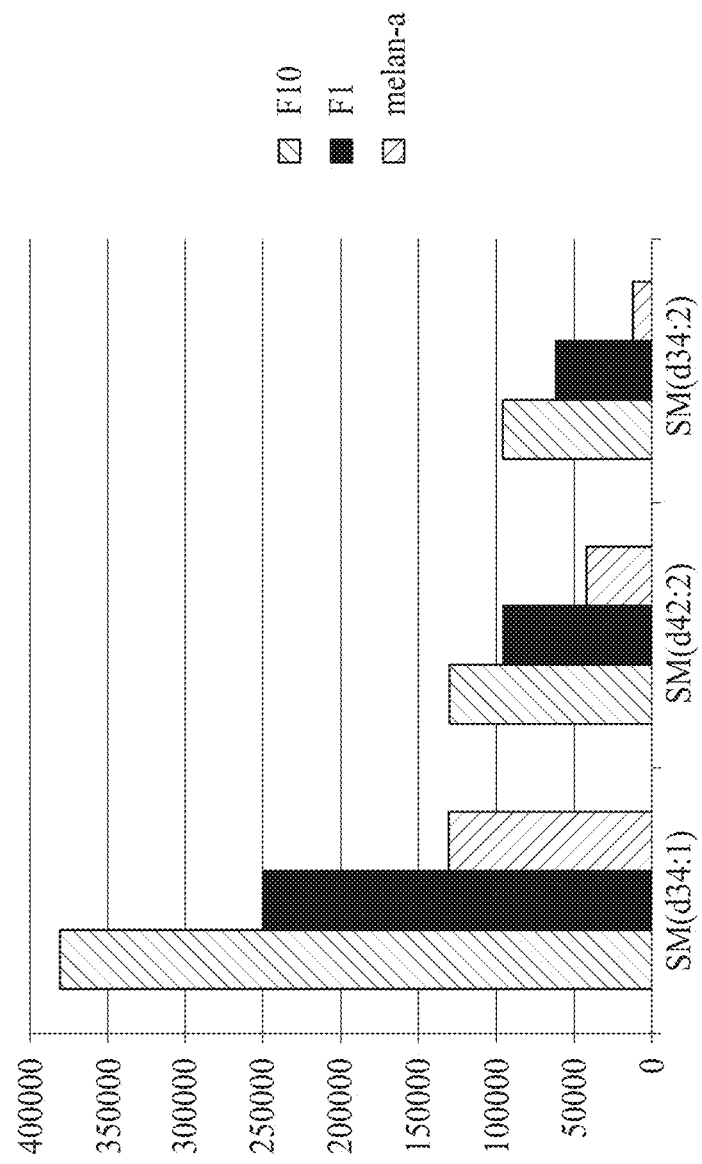

FIG. 10A
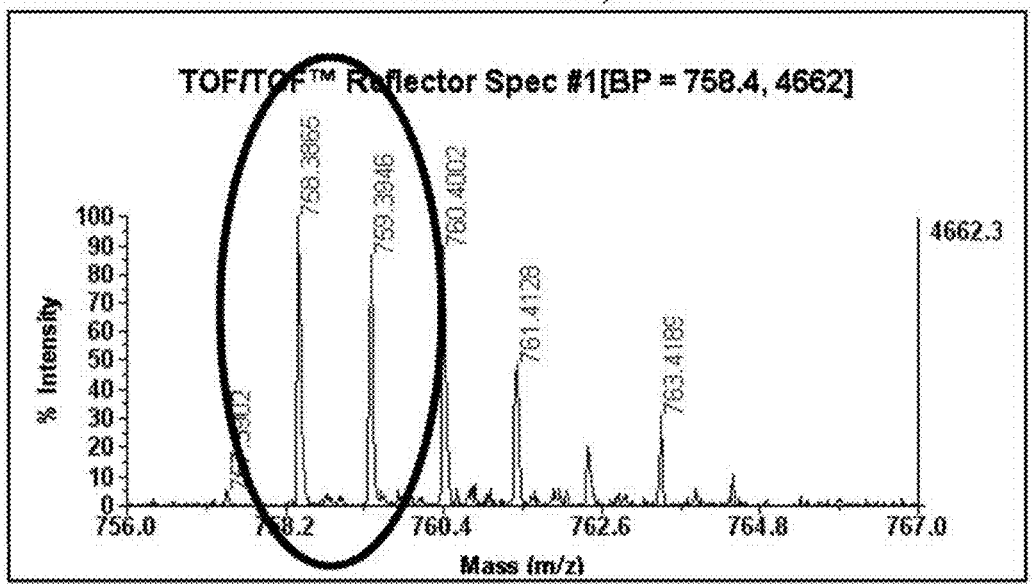
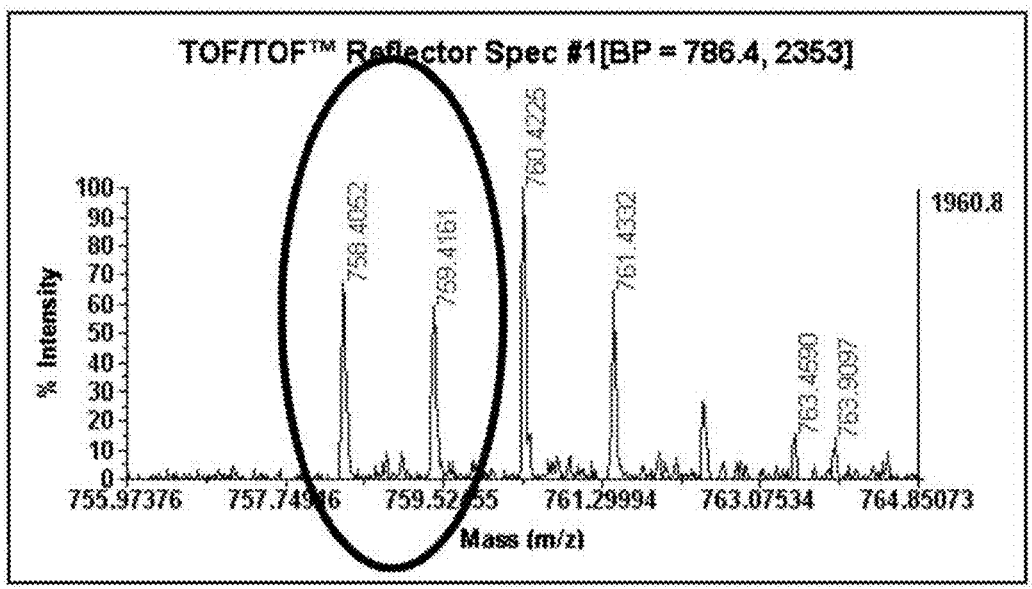

FIG. 10B (CONT.)
Large Tumor, Not Labeled
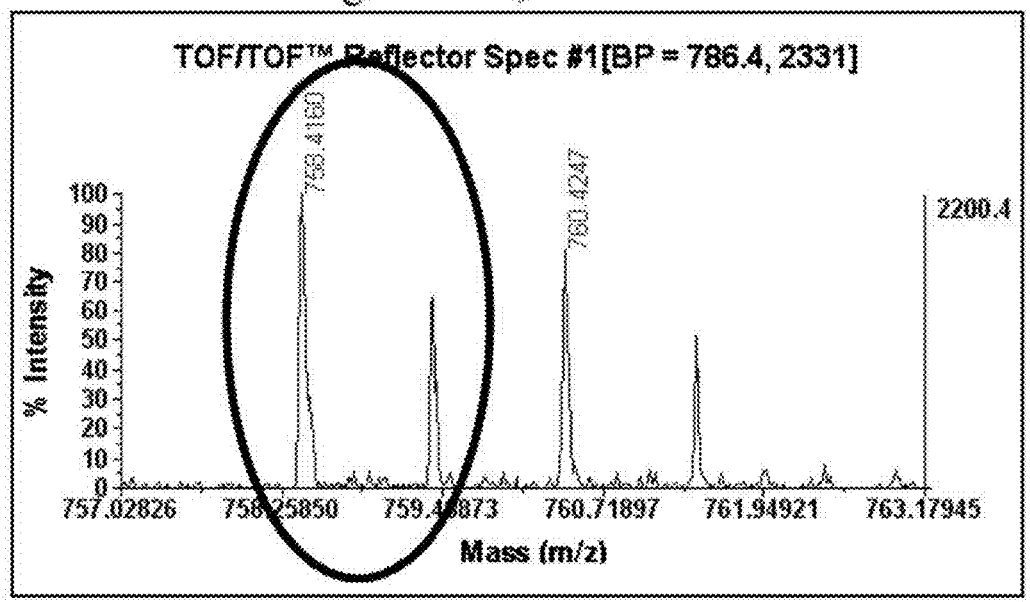
M1/M0
~0.5
~0.45
(Tumor
Extract)
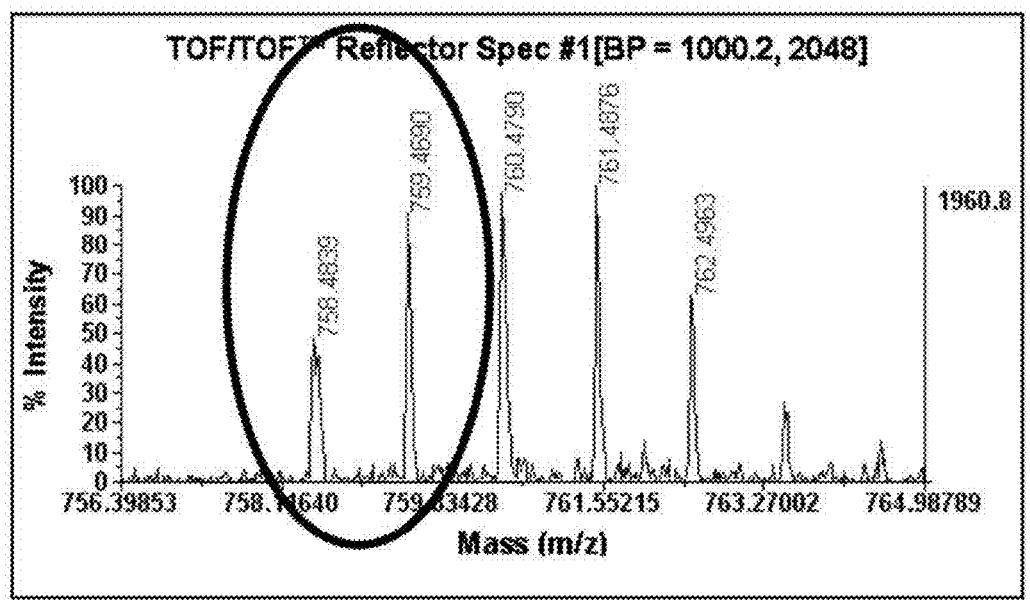
M1/M0
~2.0
~1.1
(Tumor
Extract)
Large Tumor, Labeled

USE OF LIPID PARTICLES IN MEDICAL DIAGNOSTICS

RELATED APPLICATIONS

The present application is the U.S. National Phase Under 35 U.S.C. § 371 of International Patent Application No. PCT/US2014/012790 entitled "USE OF LIPID PARTICLES IN MEDICAL DIAGNOSTICS," filed on Jan. 23, 2014, which claims priority under 35 U.S.C. § 119(e) to U.S. Provisional Patent Application No. 61/756,401 filed on Jan. 24, 2013. The content of these related applications is hereby incorporated by reference in its entirety.

STATEMENT GOVERNMENT RIGHTS

This invention was made with government support awarded by the U.S. Department of Energy under Contract No. DE-AC02-05CH11231 and by the National Institutes of Health under ICBP Grant No. U54 CA112970. The government has certain rights in the invention.

FIELD OF THE INVENTION

The present disclosure relates generally to the fields of mass spectrometry, microbiology, molecular biology, and biomedicine. More specifically, the present application relates to methods for identifying one or more diseased cells in a subject, methods for cancer diagnosis, methods for determining cancer progression in a subject and methods for assessing health status in a subject.

BACKGROUND

Exosomes, lipid bilayers, and cell membrane fragments circulate in the bloodstream and are produced in high abundance from malignant tumors. Hector Peinado, et al., in "Melanoma exosomes educate bone marrow progenitor cells toward a pro-metastatic phenotype through MET." Nat Med. 2012 Jun.; 18(6):883-91, which is hereby incorporated by reference, describe that tumor-derived exosomes are emerging mediators of tumorigenesis. Microparticles are part of the mechanism of cancer metastasis. They are comprised of and transfer, among others, proteins, lipids, mRNA, small RNA and microRNA. Proteins may indicate cancer type, with protein abundance dependent upon metastatic potential. Lipid composition of tumor-derived microparticles, however, have not yet been determined or used in an assay or diagnostic of disease. There is a need for efficient methods capable of analyzing microparticles and determining the abundance of lipids in biological samples for disease diagnosis and assessment of health status.

SUMMARY OF THE INVENTION

The present application relates to methods for identifying one or more diseased cells in a subject, methods for cancer diagnosis, methods for determining cancer progression in a subject and methods for assessing health status in a subject using lipids and nanostructure-initiator mass spectrometry.

Some embodiments disclosed herein provide a method for identifying one or more diseased cells in a subject, comprising: providing a biological sample derived from a subject, analyzing the biological sample by mass spectrometry, and determining the abundance of one or more lipids in the biological sample, wherein an altered abundance of the one or more lipids in the biological sample, as compared to a reference level, indicates a presence of one or more diseased cells in the subject from which the biological sample is derived. In some embodiments, the reference level is established using a reference sample from a healthy subject. In some embodiments, the subject is a mammal. In still other embodiments, the mammal is a human.

In some embodiments, the biological sample comprises a tissue sample, a bodily fluid, a cell culture or extracts thereof, or a combination thereof. In some embodiments, the bodily fluid comprises whole blood, blood serum, blood plasma, blood filtrate, urine, saliva, sputum, breast milk, ascites fluid, synovial fluid, amniotic fluid, semen, cerebrospinal fluid, follicular fluid and tears, or a combination thereof. In some embodiments, the tissue sample is a biopsy sample.

In some embodiments, the biological sample comprises one or more lipid-containing microparticles. In some embodiments, the one or more lipid-containing microparticles are exosomes, cell membrane fragments, cellular and intracellular organelle fragments, lipid bilayers, or a combination thereof. In some embodiments, the one or more lipid-containing microparticles have a size of no more than about 2 μm in diameter. In some embodiments, the one or more lipid-containing microparticles have a size of about 0.2 μm in diameter.

In some embodiments, analyzing the biological sample by mass spectrometry comprises isolating the one or more lipid-containing microparticles from the biological sample and analyzing the lipid-containing microparticles by mass spectrometry. In some embodiments, the isolating step comprises isolating the one or more lipid-containing microparticles from the biological sample by filtration, centrifugation, microfluidics, antibody affinity capture, or a combination thereof In some embodiments, determining the abundance of one or more lipids in the biological sample comprises determining the lipid composition of the biological sample.

In some embodiments, at least one of the one or more lipids is a monounsaturated glycerolipid. In some embodiments, at least one of the one or more lipids is a monounsaturated lipid or a saturated lipid. In some embodiments, at least one of the one or more lipids is a highly saturated lipid detected by mass spectrometry at about m/z 760. In some embodiments, at least one of the one or more lipids comprises a lipid detected by mass spectrometry at about m/z 788.616, at about m/z 734.569, at about m/z 732.554, at about m/z 703.575, at about m/z 758.569, at about m/z 758.600, at about m/z 760.585, at about m/z 746.569, at about m/z 746.606, about m/z 782.569, about m/z 762.601, at about m/z 706.538, about m/z 782.569, at about m/z 808.585, at about m/z 724.528, at about m/z 496.340, at about m/z 701.559, at about m/z 790.559, at about m/z 744.554, at about m/z 813.684, at about m/z 718.538, at about m/z 700.572, at about m/z 716.522, at about m/z 786.601, at about m/z 782.569, at about m/z 774.601, at about m/z 750.543, at about m/z 784.666, at about m/z 810.682, at about m/z 702.543, or a combination thereof. In some embodiments, at least one of the one or more lipids comprises a lipid detected by mass spectrometry at about m/z 648.6304, at about m/z 538.5207, at about m/z 722.5574, at about m/z 700.5739, at about m/z 756.6337, at about m/z 778.6181, at about m/z 810.6781, at about m/z 832.6667, at about m/z 784.6613, at about m/z 806.6432, at about m/z 812.6909, at about m/z 834.679337, at about m/z 496.3414, at about m/z 524.373, at about m/z 522.3571, at about m/z 546.3553, at about m/z 454.294, at about m/z 482.3278, at about m/z 480.3097, at about m/z 678.508, at about m/z 676.4939, at about m/z 674.4662, at about m/z 706.5404, at about m/z 734.5717, at about m/z 732.5562, at about m/z 730.5439, at about m/z 728.5267, at about m/z 762.6029, at about m/z 760.5881, at about m/z 758.5715, at about m/z 756.5589, at about m/z 754.5394, at about m/z 788.6188, at about m/z 786.6026, at about m/z 784.5883, at about m/z 782.5723, at about m/z 810.605, at about m/z 808.5852, at about m/z 806.5714, at about m/z 834.6105, at about m/z 832.5859, at about m/z 692.5608, at about m/z 718.5761, at about m/z 746.6074, at about m/z 690.5083, at about m/z 720.5563, at about m/z 716.5241, at about m/z 746.5716, at about m/z 744.5557, at about m/z 742.5397, at about m/z 774.6024, at about m/z 772.5866, at about m/z 770.5705, at about m/z 768.554, at about m/z 766.5399, at about m/z 674.5134, at about m/z 704.555, at about m/z 702.5451, at about m/z 700.5293, at about m/z 730.5768, at about m/z 728.5592, at about m/z 726.5444, at about m/z 724.5292, at about m/z 758.6063, at about m/z 754.5757, at about m/z 752.5608, at about m/z 752.5595, at about m/z 750.5451, at about m/z 748.531, at about m/z 784.628, at about m/z 778.5781, at about m/z 776.5621, at about m/z 774.5456, at about m/z 689.5612, at about m/z 711.5457, at about m/z 749.5355, at about m/z 766.5602, at about m/z 747.5208, at about m/z 764.5472, at about m/z 777.566, at about m/z 794.5945, at about m/z 775.5505, at about m/z 792.5765, at about m/z 762.5297, at about m/z 790.5614, at about m/z 788.5477, at about m/z 838.5617, at about m/z 836.5452, at about m/z 675.5451, at about m/z 705.5839, at about m/z 703.5774, at about m/z 731.6081, at about m/z 815.7008, at about m/z 732.6077, at about m/z 787.6636, at about m/z 813.6856, at about m/z 835.6672, at about m/z 835.6659, at about m/z 701.5613, or a combination thereof.

In some embodiments, the mass spectrometry is nanostructure-initiator mass spectrometry (NIMS). In some embodiments, the mass spectrometry is liquid chromatography/mass spectrometry (LC/MS).

In some embodiments, the disease is cancer. In some embodiments, the cancer is a benign tumor, malignant tumor, solid tumor, breast cancer, prostate cancer, ovarian cancer, gynecological cancer, melanoma, pancreatic cancer, lung cancer, head and neck squamous cell carcinoma, bone cancer, brain cancer, or a combination thereof.

Some of the embodiments disclosed herein provide a method for cancer diagnosis, comprising: providing a biological sample derived from a subject, analyzing the biological sample by mass spectrometry, and determining the abundance of one or more lipids in the biological sample, wherein an altered abundance of the one or more lipids in the biological sample, as compared to a reference lipid abundance level, is indicative of a cancer in the subject. In some embodiments, the reference level is established using a reference sample from a healthy subject.

Some embodiments described herein provide a method for determining cancer progression in a subject. The method can, in some embodiments, include (a) analyzing a biological sample derived from the subject by mass spectrometry; (b) determining the abundance of one or more lipids in the biological sample; (c) repeating steps (a) and (b) at least one time at a different time point; and (d) comparing the abundance of at least one of the one or more lipids in the biological samples at different time points, wherein a change in the abundance of at least one of the one or more lipids is indicative of a change in cancer progression in the subject. In some embodiments, the subject is undergoing or has undergone cancer treatment.

Some of the embodiments disclosed herein provide a method for assessing health status of a subject. The method can, in some embodiments, include: (a) administering to a subject a stable isotope; (b) obtaining a biological sample from a subject; (c) analyzing the biological sample or a derivative thereof by mass spectrometry; and (d) determining the rate and/or amount of stable isotope incorporation for one of more lipids in the biological sample or the derivative thereof, wherein an altered rate and/or amount of stable isotope incorporation in the one or more lipids as compared to a reference rate and/or amount of stable isotope incorporation is indicative of the health status of the subject. In some embodiments, the reference level is established using a reference sample from a healthy subject. In some embodiments, the stable isotope is deuterium.

BRIEF DESCRIPTION OF THE DRAWINGS

FIG. 3A depicts nanostructure-initiator mass spectrometry (NIMS) spectra showing lipid profiles of purified F10 exosome and crude F10 filtered supernatant.

FIG. 4 depicts scatterplots showing differences in lipid composition between exosomes from different cancer cell lines and varying with metastatic potential (through n=1).

FIG. 8A is a bar graph showing relative abundance of glucosylceramide lipids in exosomes derived from F10, F1 and non-metastatic cells.

FIG. 8B is a bar graph showing relative abundance of sphingomyelin (SM) lipids in exosomes derived from F10, F1 and non-metastatic cells.

FIG. 11 depicts digital images of heterogeneous spatial distribution of lipids in labeled and unlabeled populations.

DETAILED DESCRIPTION

Figure 1:
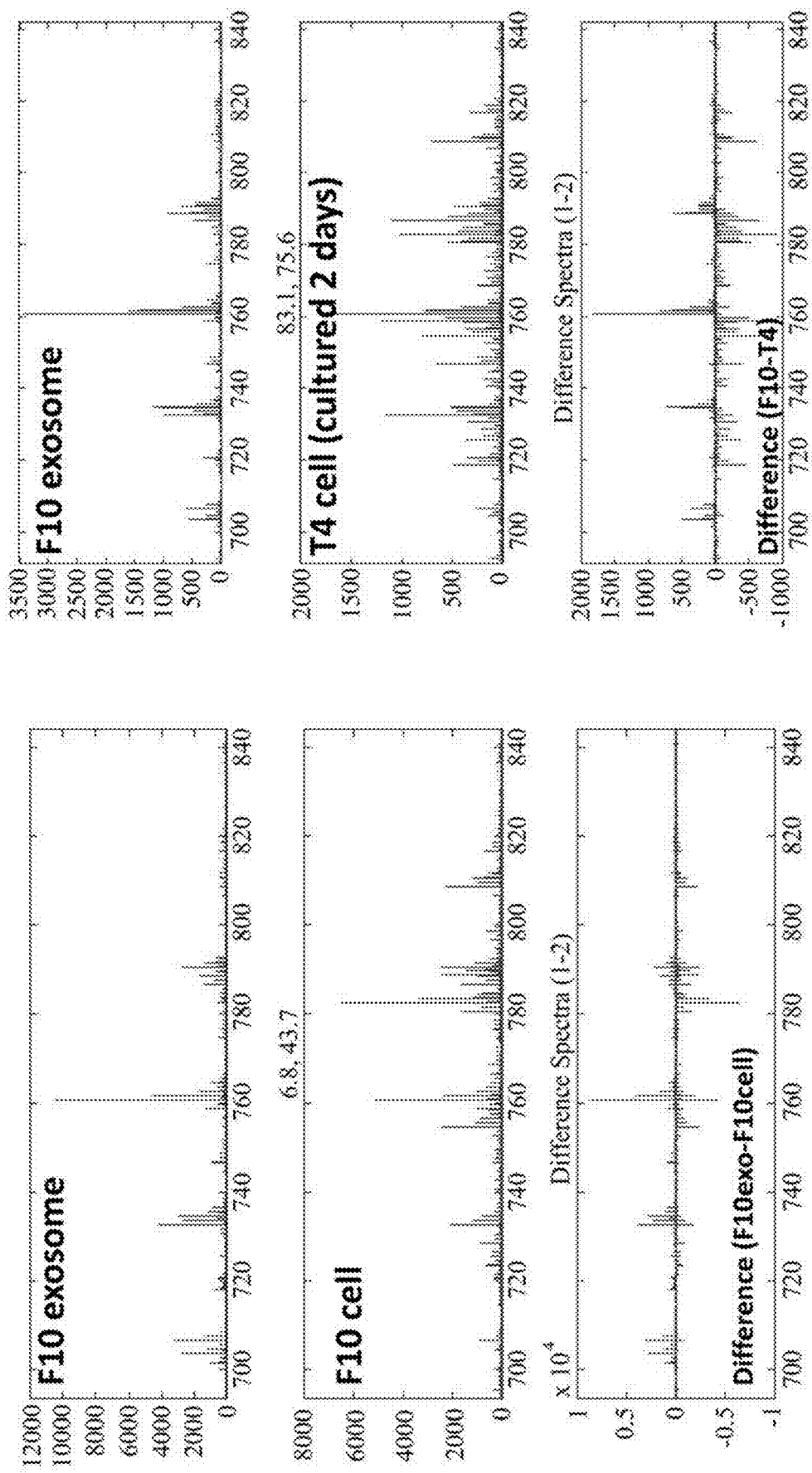
FIG. 1 depicts nanostructure-initiator mass spectrometry (NIMS) spectra showing lipid profiles of F10 exosomes from melanoma cells, F10 melanoma cells, and invasive breast cancer cells.

The description that follows illustrates various embodiments of the subject matter disclosed herein. Those of skill in the art will recognize that there are numerous variations and modifications of the subject matter provided herein that are encompassed by its scope. Accordingly, the description of certain embodiments should not be deemed to limit the scope of the present application.

In addition, in the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are contemplated and make part of this disclosure.

The present application relates to methods for disease diagnosis and methods for assessment of health status in a subject by analyzing the abundance of one or more lipids in a biological sample. In some embodiments, the biological sample comprises lipid-containing microparticles. For example, the method can be used to determine the presence or absence of one or more diseased cells in a subject, or for disease diagnosis such as proliferative diseases. In some embodiments, the diseased cell can be a tumor cell.

Methods for identifying one or more disease cells in a subject are provided herein. In some embodiments, the presence of one or more diseased cells in a subject can be identified by providing a biological sample derived from a subject, analyzing the biological sample by mass spectrometry, and determining the abundance of one or more lipids in the biological sample, wherein an altered abundance of the one or more lipids in the biological sample, as compared to a reference level, indicates a presence of one or more diseased cells in the subject from which the biological sample is derived. In some embodiments, the biological sample comprises one or more lipid-containing microparticles, for example lipid-containing microparticles that comprise at least one of the one or more lipids.

Also disclosed herein are methods for cancer diagnosis. The method can, in some embodiments, include providing a biological sample derived from a subject, analyzing the biological sample by mass spectrometry, and determining the abundance of one or more lipids in the biological sample, wherein an altered abundance of the one or more lipids in the microparticles, as compared to a reference level, is indicative of a cancer in the subject.

Methods for determining the extent of cancer progression in a subject are also provided herein. In some embodiments, the method includes (a) analyzing a biological sample derived from the subject by mass spectrometry, (b) determining the abundance of one or more lipids in the biological sample, (c) repeating steps (a) and (b) at least one time at a different time point and (d) comparing the abundance of at least one of the one or more lipids in the biological samples at different time points, wherein a change in the abundance of at least one of the one or more lipids is indicative of a change in cancer progression in the subject. In some embodiments, the subject is undergoing or has undergone a cancer treatment so that the method can be used to determine the efficacy of the cancer treatment.

Methods for assessing health status in a subject are also provided herein. In some embodiments, the method includes administering to a subject a stable isotope, obtaining a biological sample from the subject, analyzing the biological sample or a derivative thereof by mass spectrometry, and determining the rate and/or amount of stable isotope incorporation in one or more lipids in the biological sample or the derivative thereof. The rate and/or amount of stable isotope incorporation in the one or more lipids in the biological sample or the derivative thereof can be compared to a reference rate and/or amount, and a difference in the determined rate (and/or amount) and the reference rate (and/or amount) is indicative of the health status of the subject. In some embodiments, the stable isotope can be deuterium.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

As used herein, the terms "lipid" includes synthetic or naturally-occurring compounds which are generally amphipathic and biocompatible. Lipids typically comprise a hydrophilic component and a hydrophobic component. Examples of lipids include, but are not limited to fatty acids, neutral fats, phosphatides, cholesterol, cholesterol esters, triglycerides, glycolipids, glycerolipids, phospholipids, glycerophospholipids, sphingolipids, sterol lipids, prenol lipids, saccharolipids, polyketides, choline glycerophospholipid, ethanolamine glycerophospholipid, phosphatidylinositol, phosphatidylglycerol, phosphatidylserine, lyso-choline glycerophospholipid, lyso-ethanolamine glycerophospholipid, phosphatidic acid, lyso-phosphatidic acid, sphingomyelin, galactosylceramide, glucosylceramide, sulfatide, free fatty acids, prostaglandins, triacylglycerol, diacylglycerol, monoacylglycerol, acyl-CoA, acylcarnitine, oxysterol, ceramide, cardiolipin, sphingoid base-1-phosphate, shingosine, lyso-sphingomyelin, gangliosides, plasmalogen, sulfatide, ceramide, low density lipoproteins (LDLs), very low density lipoproteins (VLDLs), high density lipoproteins (HDLs), sphingoid base-1-phosphates or derivatives thereof.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, "abundance" can refer to the absolute amount of one or more lipids in a biological sample, the relative amount of one or more lipids in a biological sample or a normalized amount of one or more lipids in a biological sample.

ABBREVIATION

SM=sphingomyelin
PS=phosphoserine
PE=phosphoethanolamine
PC=phosphocholine

Biological Samples

The term "biological sample", as used herein, includes, without limitation, cell cultures or extracts thereof; tissue samples (e.g., biopsied material obtained from a subject) or extracts thereof; and body fluids (e.g., blood, saliva, urine, feces, semen, tears, or other body fluids) or extracts thereof. The methods disclosed herein can be used to analyze various biological samples. The biological sample can, in some embodiments, contain lipid-containing microparticles. For example, the biological sample can be a tissue sample or extracts thereof, a bodily fluid or extracts thereof, or a cell culture or extracts thereof. Examples of a cell culture or extracts thereof include, but are not limited to, cells, cell pellets, lysed cells, raw cell lysis, filtered cell lysis, cell culture supernatant, or a combination thereof. Non-limiting examples of the bodily fluid can include whole blood, blood serum, blood plasma, blood filtrate, urine, saliva, sputum, breast milk, ascites fluid, synovial fluid, amniotic fluid, semen, cerebrospinal fluid, follicular fluid, tears, or a combination thereof. In some embodiments, the biological sample is blood filtrate. In some embodiments, the biological sample is a biopsy sample or a derivative thereof. In some embodiments, the biological sample comprises cells from a cell culture derived from a tissue or cell sample obtained from a patient or a healthy subject. In some embodiments, the biological sample is a cell culture supernatant. In some embodiments, the biological sample is a cell pellet. In some embodiments, a cell pellet can be formed by centrifugation. In some embodiments, any portion of a cell culture can be analyzed, including for example a cell culture supernatant or a cell pellet.

In some embodiments, the biological sample can include, but are not limited to, low metastatic cancer cells (e.g., F1 cells), high metastatic cancer cells (e.g., F10 cells), non-metastatic cells (e.g., non-metastatic cancer cells), exosomes derived from low metastatic cells, exosomes derived from high metastatic cells, or exosomes derived from non-metastatic cells, or other lipid-containing microparticles (e.g., membrane fragments, lipid bilayers, intracellular membrane fragments) derived from low metastatic cancer cells, high metastatic cancer cells or non-metastatic cells. The cells can be cells directly taken from a patient or a healthy subject. The cells can also be cultured cells that derived from the patient or healthy subject. In some embodiments, the biological sample can include cell pellets from cell culture of low metastatic cancer cells (e.g., F1 cells), high metastatic cancer cells (e.g., F10 cells), or non-metastatic cells, and/or filtered supernatant from cell culture of low metastatic cancer cells (e.g., F1 cells), high metastatic cancer cells (e.g., F10 cells), or non-metastatic cells. In some embodiments, samples can comprise exosomes isolated from cancer cell lines, as well as from Dulbecco's modified Eagle's medium (DMEM). In some embodiments, the biological sample comprises invasive breast cancer cells. In some embodiments, the biological sample comprises melanoma cells.

The biological sample, in some embodiments, can comprise one or more microparticles, for example lipid-containing microparticles. In some embodiments, the lipid-containing microparticles can include exosomes, cell membrane fragments, lipid bilayers, or a combination thereof. In some embodiments, the microparticles can be isolated from the biological sample. The isolating step can include, for example, isolating the one or more microparticles from the biological sample by filtration, centrifugation, microfluidics, antibody affinity capture, or a combination thereof. The microparticles, in some embodiments, are analyzed by mass spectrometry to determine the abundance of one or more lipids therein.

The size of the microparticles (for example, the lipid-containing microparticles) described herein is not particularly limited. For example, the microparticles can be about 0.2 μm to about 2 μm in diameter. In some embodiments, the microparticles can be about 0.2 μm, about 0.3 μm, about 0.4 μm, about 0.5 μm, about 0.6 μm, about 0.7 μm, about 0.8 μm, about 0.9 μm, about 1.0 μm, about 1.1 μm, about 1.2 μm, about 1.3 μm, about 1.4 μm, about 1.5 μm, about 1.6 μm, about 1.7 μm, about 1.8 μm, about 1.9 μm, about 2 μm, or a range between any two of these values, in diameter. In some embodiments, the microparticles can be about 0.2 μm in diameter. In some embodiments, the microparticles can have a size of no more than about 2 μm in diameter.

Mass Spectrometry

In the methods described herein, a biological sample or one or more microparticles from the biological sample (e.g., lipid-containing microparticles) can be analyzed by mass spectrometry (MS)-based technologies for determining the abundance of one or more lipids in the biological sample or the microparticles. The MS-based technologies can be used to perform high-throughput assays for determining the lipid abundance in the biological sample or the microparticles. The abundance of one or more lipids can be analyzed using a mass spectrometry analysis whereby individual lipids can be identified by specific peaks in the MS spectra. Suitable analysis methods may include but are not limited to matrix-assisted laser desorption ionization (MALDI), nanoparticle initiator mass spectrometry (NIMS), liquid chromatography/mass spectrometry (LC/MS) and secondary ion mass spectrometry (SIMS) and gas chromatography/mass spectrometry (GC/MS); Laser Desorption; Desorption ElectroSpray Ionization (DESI); Probe ElectroSpray Ionization (PESI); or Laser Spray. Various instrument modalities may include but are not limited to time-of-flight (TOF), Orbitrap, Fourier-transform ion cyclotron (FTIR), magnetic sector, quadrupole, or other mass spectrometers. In some embodiments, tandem mass spectrometers (MS/MS) are used, such as TOF-TOF or Quadrupole-TOF, wherein the second MS collects fragmentation spectra for molecular characterization of ions analyzed by the first mass spectrometer.

In some embodiments, the mass of the lipids can be determined by nanostructure-initiator mass spectrometry (NIMS). NIMS is described in T. R. Northen, O. Yanes, M. T. Northen, D. Marrinucci, W. Uritboonthai, J. Apon, S. L. Golledge, A. Nordstrom, G. Siuzdak, *Nature* 2007, 449, 1033-1036; T. R. Northen, J. C. Lee, L. Hoang, J. Raymond, D. R. Hwang, S. M. Yannone, C. H. Wong, G. Siuzdak, *Proc. Natl. Acad. Sci. USA* 2008, 105, 3678-3683; and U.S. Patent Application Publication Nos. 2008/0128608 and 2012/0225797, which are herein fully incorporated by reference. Production of NIMS chips is described in detail in H. K. Woo, T. R. Northen, O. Yanes, G. Siuzdak, *Nat. Protoc.* 2008, 3, 1341-1349, which is herein fully incorporated by reference.

A variety of apparatuses can be used in NIMS to measure the mass-to-charge ratio of the ionized target. For example, in several embodiments a time-of-flight mass analyzer is used for measuring the desorbed and ionized target. However, other non-limiting examples of mass analyzers that can be used include magnetic ion cyclotron resonance instruments, deflection instruments, and quadrupole mass analyzers.

For analysis of the biological samples, small samples volumes (e.g., one microliter and below) can be applied to (e.g., spotted onto) a mass spectrometry surface (e.g., a NIMS chip surface). In some embodiments, the biological sample is a MeOH-extracted sample. In the case of a NIMS chip, the nanostructured chip can be, in some embodiments, coated with ultrathin liquid layers of perfluorinated (di)

siloxanes. A tag comprising a fluorous tail can interact with the chip surface via fluorous-phase-interactions, so that a tagged sample can stay on the chip surface. In a "chromatographic" step, all other components of the sample that do not interact with the chip surface can be washed away, or simply be pipetted off, while the reaction product sticks to the surface. Analysis of lipid composition in the mass spectrometer can be performed based on the presence and abundance of the lipid ions. In some embodiments, an internal standard (e.g., an isotope labeled compound or an analog for the reaction product) is used for determining the presence and abundance of the lipid.

In some embodiments, lipids are linked to tags that can interact with a mass spectrometry (MS) surface, for example surface of a NIMS chip. For example, the substrate can be linked to a perfluorinated tag that is capable of interacting with a MS surface (e.g., NIMS chip surface) having a perfluorinated coat.

Use of Mass Spectrometry for Analyzing Lipid Profiles for Biological Samples

As described herein, mass spectrometry (e.g., NIMS and LC/MS) can be used to analyze the abundance of one or more lipids in a biological sample. In some embodiments, analyzing the abundance of one or more lipids in a biological sample comprises determining the lipid profile of the biological sample. As used herein, the lipid profile of a biological sample can be, for example, the absolute amount or a relative amount of one or more lipids in the biological sample. In some embodiments, the abundance of two or more lipids (for example the 5-100 most abundant lipids in the biological sample) in a biological sample is determined.

In some embodiments, determining the abundance of lipids in the biological sample (for example, a biological sample containing lipid-containing microparticles) can include determining the lipid composition of the microparticles. Various lipids can be analyzed (e.g., for abundance) by mass spectrometry. For example, the lipid can be a highly saturated lipid (e.g., a saturated lipid or a monounsaturated lipid) or a polyunstaturated lipid. In some embodiments, the lipid can be a monounsaturated lipid (e.g., a monounsaturated glycerolipid). In some embodiments, the lipid can be a monounsaturated lipid or a saturated lipid. In some embodiments, the lipid is a highly saturated lipid detected by mass spectrometry at about m/z 760.

In some embodiments, one or more stable isotopes can be used to label lipids and the rate and/or amount of stable isotope incorporation for the lipids can be determined by MS. The rate and/or amount of stable isotope incorporation of a lipid can, for example, correlate with the turnover rate of the lipid. The rate and/or amount of stable isotope incorporation of a lipid can also, for example, correlate with the fraction of the newly synthesized lipid. In some embodiments, the rate and/or amount of stable isotope incorporation of a lipid is positively correlated with the turnover rate of the lipid. In some embodiments, the rate and/or amount of stable isotope incorporation of a lipid is positively correlated with the fraction of the newly synthesized lipid.

Many types of lipids can be analyzed (e.g., for abundance) by mass spectrometry, including but not limited to, a fatty acid lipid, a glycerolipid, a phosphatidylserine, a glycerophospholipid, a sphingolipid, a phosphatidylglycerol, a ceramide, a palmitoylsphingosine, a phospholipid (e.g., a phospholipid comprising phosphoserine, phosphoethanolamine, and/or phosphocholine), a prenol lipid, a saccharolipid, a polyketide, a ceramide, a diacylglycerol, a triglyceride, a glycosylceramide (e.g., a glucosylceramide and a galactosylceramide), a lysophosphoethanolamine, a lysophosphocholine, and any combination thereof. In some embodiments, the sphingolipid can be sphingomyelin. In some embodiments, the phospholipid can be phosphoserine, phosphoethanolamine, phosphocholine, or a combination thereof. In some embodiments, the lipid is a saturated glycerolipid or a monounsaturated glycerolipid. In some embodiments, the lipid is a ceramide. In some embodiments, the lipid is a saturated or monounsaturated lipid detected by mass spectrometry (e.g., LC-MS) at about m/z 788.616, at about m/z 734.569, at about m/z 732.554, at about m/z 703.575, at about m/z 758.569, at about m/z 758.600, at about m/z 760.585, at about m/z 746.569, at about m/z 746.606, about m/z 782.569, about m/z 762.601, at about m/z 706.538, about m/z 782.569, at about m/z 808.585, at about m/z 724.528, at about m/z 496.340, at about m/z 701.559, at about m/z 790.559, at about m/z 744.554, at about m/z 813.684, at about m/z 718.538, at about m/z 700.572, at about m/z 716.522, at about m/z 786.601, at about m/z 782.569, at about m/z 774.601, at about m/z 750.543, at about m/z 784.666, at about m/z 810.682, at about m/z 702.543, or a combination thereof. In some embodiments, the lipid is a lipid detected by mass spectrometry (e.g., LC-MS) at about m/z 648.6304, at about m/z 538.5207, at about m/z 722.5574, at about m/z 700.5739, at about m/z 756.6337, at about m/z 778.6181, at about m/z 810.6781, at about m/z 832.6667, at about m/z 784.6613, at about m/z 806.6432, at about m/z 812.6909, at about m/z 834.679337, at about m/z 496.3414, at about m/z 524.373, at about m/z 522.3571, at about m/z 546.3553, at about m/z 454.294, at about m/z 482.3278, at about m/z 480.3097, at about m/z 678.508, at about m/z 676.4939, at about m/z 674.4662, at about m/z 706.5404, at about m/z 734.5717, at about m/z 732.5562, at about m/z 730.5439, at about m/z 728.5267, at about m/z 762.6029, at about m/z 760.5881, at about m/z 758.5715, at about m/z 756.5589, at about m/z 754.5394, at about m/z 788.6188, at about m/z 786.6026, at about m/z 784.5883, at about m/z 782.5723, at about m/z 810.605, at about m/z 808.5852, at about m/z 806.5714, at about m/z 834.6105, at about m/z 832.5859, at about m/z 692.5608, at about m/z 718.5761, at about m/z 746.6074, at about m/z 690.5083, at about m/z 720.5563, at about m/z 716.5241, at about m/z 746.5716, at about m/z 744.5557, at about m/z 742.5397, at about m/z 774.6024, at about m/z 772.5866, at about m/z 770.5705, at about m/z 768.554, at about m/z 766.5399, at about m/z 674.5134, at about m/z 704.555, at about m/z 702.5451, at about m/z 700.5293, at about m/z 730.5768, at about m/z 728.5592, at about m/z 726.5444, at about m/z 724.5292, at about m/z 758.6063, at about m/z 754.5757, at about m/z 752.5608, at about m/z 752.5595, at about m/z 750.5451, at about m/z 748.531, at about m/z 784.628, at about m/z 778.5781, at about m/z 776.5621, at about m/z 774.5456, at about m/z 689.5612, at about m/z 711.5457, at about m/z 749.5355, at about m/z 766.5602, at about m/z 747.5208, at about m/z 764.5472, at about m/z 777.566, at about m/z 794.5945, at about m/z 775.5505, at about m/z 792.5765, at about m/z 762.5297, at about m/z 790.5614, at about m/z 788.5477, at about m/z 838.5617, at about m/z 836.5452, at about m/z 675.5451, at about m/z 705.5839, at about m/z 703.5774, at about m/z 731.6081, at about m/z 815.7008, at about m/z 732.6077, at about m/z 787.6636, at about m/z 813.6856, at about m/z 835.6672, at about m/z 835.6659, at about m/z 701.5613, or a combination thereof.

In some embodiments, the lipids can include PC(34:1) detected at about m/z 788.616, PC(32:1) detected at about m/z 734.569, PC(32:0) detected at about m/z 732.554, SM(d34:1) detected at about m/z 703.575, PC(36:2)

detected at about m/z 758.569, PC(36:1) detected at about m/z 758.600, PC(30:0) detected at about m/z 760.585, PE(36:2) detected at about m/z 746.569, PC(36:4) detected at about m/z 746.606, about m/z 782.569 and about m/z 762.601, PC(34:2) detected at about m/z 706.538 and about m/z 782.569, PC(P-34:0) detected at about m/z 808.585, PE(P-34:1) detected at about m/z 724.528, LysoPC(16:0) detected at about m/z 496.340, SM(d42:2) detected at about m/z 701.559, PS(36:1) detected at about m/z 790.559, PE(34:1) detected at about m/z 744.554, SM(d34:2) detected at about m/z 813.684, PE(36:1) detected at about m/z 718.538, Glucosylceramide (d18:1/16:0) detected at about m/z 700.572, PE(P-38:5) detected at about m/z 716.522, PC(34:0) detected at about m/z 786.601, PC(38:5) detected at about m/z 782.569, PE(P-36:4) detected at about m/z 774.601, PE(38:1) detected at about m/z 750.543, Glucosylceramide (d18:1/22:0) detected at about m/z 784.666, Glucosylceramide (d18:1/24:1) detected at about m/z 810.682, PE(34:2) detected at about m/z 702.543, LysoPC (18:1(11Z)) detected at about m/z 522.355, or a combination thereof.

The abundance of one or more lipids in a biological sample can be used to determine the presence or absence of one or more disease cells in the subject from which the biological sample is derived. For example, the abundance of one or more lipids in the biological sample can be compared to a reference level and an altered abundance in the biological sample is indicative of the presence of one or more disease cells in the subject. The subject having one or more disease cells can have lower or higher level of abundance of the one or more lipids as compared to the reference level. The reference level can be an abundance level of the one or more lipids in a healthy subject or a subject free of the disease of interest. The reference level can, in some embodiments, be derived from a parallel experiment conducted on a biological sample obtained from the healthy subject or a subject free of the disease of interest. In yet other embodiments, the reference level is a value obtained previously for the abundance level of the one or more lipids in a healthy subject or a subject free of the disease of interest. For example, the reference level can be a value from a database.

The disease can, in some embodiments, be a proliferative disease (such as cancer). Non-limiting examples of cancer or proliferative disorders include a benign or malignant tumor; solid tumor; carcinoma of the brain, kidney, liver, adrenal gland, bladder, breast, and stomach; gastric tumors, cancer of ovaries, colon, rectum, prostate, pancreas, lung, vagina, cervix, testis, genitourinary tract, esophagus, larynx, skin, bone, and thyroid; sarcoma; glioblastomas; neuroblastomas; multiple myeloma; gastrointestinal cancer, for example colon carcinoma or colorectal adenoma; tumor of the neck and head; an epidermal hyperproliferation; psoriasis; prostate hyperplasia; neoplasia, for example neoplasia of epithelial character; adenoma; adenocarcinoma; keratoacanthoma; epidermoid carcinoma; large cell carcinoma; non-small-cell lung carcinoma; lymphomas; Hodgkins and Non-Hodgkins; mammary carcinoma; follicular carcinoma; undifferentiated carcinoma; papillary carcinoma; seminoma; melanoma; Smoldering of indolent multiple myeloma; and hematological malignancies (for example leukemia, diffuse large B-cell lymphoma (DLBCL), activated B-cell like (ABC) DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, and intravascular large B-cell lymphoma).

In some embodiments, the abundance of one or more lipids in a biological sample can be used to diagnose cancer. For example, the abundance of one or more lipids in a biological sample from a subject suspected of having cancer can be compared to a reference level and an altered abundance in the biological sample indicates that the subject have cancer. The subject suffering from cancer can have a lower or higher level of abundance of the one or more lipids as compared to the reference level. The reference level can be an abundance level of the one or more lipids in a healthy subject or a subject free of cancer. The reference level can, in some embodiments, be derived from a parallel experiment conducted on a biological sample obtained from the healthy subject or a subject free of cancer. In yet other embodiments, the reference level is a value obtained previously for the abundance level of the one or more lipids in a healthy subject or a subject free of cancer. For example, the reference level can be a value from a database.

As described herein, a number of lipids are associated with cancer metastasis, including highly saturated lipids (e.g., a saturated lipid or a monounsaturated lipid). Examples of lipids that are associated with cancer metastasis include, but are not limited to, a lipid (e.g., a saturated or monounsaturated lipid) that is detected by mass spectrometry at about m/z 788.616, at about m/z 734.569, at about m/z 732.554, at about m/z 703.575, at about m/z 758.569, at about m/z 758.600, at about m/z 760.585, at about m/z 746.569, at about m/z 746.606, about m/z 782.569, about m/z 762.601, at about m/z 706.538, about m/z 782.569, at about m/z 808.585, at about m/z 724.528, at about m/z 496.340, at about m/z 701.559, at about m/z 790.559, at about m/z 744.554, at about m/z 813.684, at about m/z 718.538, at about m/z 700.572, at about m/z 716.522, at about m/z 786.601, at about m/z 782.569, at about m/z 774.601, at about m/z 750.543, at about m/z 784.666, at about m/z 810.682, at about m/z 702.543, or a combination thereof. In some embodiments, the cancer-associating lipid is a highly saturated lipid detected by mass spectrometry at about m/z 760. In some embodiments, the cancer-associating lipid can be, for example, a fatty lipid, a glycerolipid, a phosphatidylserine, a glycerophospholipid, a sphingolipid (e.g., sphingomyelin), a phospholipid (e.g., a phospholipid comprising phosphoserine, phosphoethanolamine, and/or phosphocholine), a prenol lipid, a saccharolipid, a polyketide, a glucosylceramide, a ceramide, or a combination thereof. In some embodiments, the cancer-associating lipid is a saturated glycerolipid or a monounsaturated glycerolipid. One or more of cancer-associating lipids can be analyzed by mass spectrometry to determine the presence or absence of cancer cells in a subject or to diagnose cancer in a subject. In some embodiments, the cancer-associating lipid is a ceramide.

Also disclosed herein are methods for monitoring the progression of a disease (e.g., cancer progression). In some embodiments, a method for determining cancer progression in a subject is provided. The method can include: (a) analyzing a biological sample derived from the subject by mass spectrometry; (b) determining the abundance of one or more lipids in the biological sample; (c) repeating steps (a) and (b) at least one time at a different time point; and (d) comparing the abundance of at least one of the one or more lipids in the biological samples at different time points, wherein a change in the abundance of at least one of the one or more lipids is indicative of a change in cancer progression in the subject. For example, a sample can be obtained from a cancer patient at a first time point, and then another sample can be obtained from the cancer patient at a second time point. The abundance of one or more lipids in the biological samples obtained from the cancer patient at different time can be analyzed by mass spectrometry and then compared to determine whether there is any change in the abundance of the one or more lipids. A change in the abundance level indicates a change in cancer progression in the patient. In some embodiments, the abundance level for a lipid in a later stage of cancer progression is higher than the abundance level in an earlier stage of cancer progression. In some embodiments, the abundance level for a lipid in a later stage of cancer progression is lower than the abundance level in an earlier stage of cancer progression. For example, the abundance level for a lipid in a low metastatic sample can be higher than the abundance level in a high metastatic sample. Or, the abundance level for a lipid in a low metastatic sample progression is lower than the abundance level in a high metastatic sample.

In some embodiments, the methods disclosed herein can be used to monitor the remission of a disease. In some embodiments, the methods disclosed herein can be used to monitor a change in a disease status of a subject. In some embodiments, the subject is undergoing or has undergone a treatment, and thus monitoring the change in the disease status of the subject can be used to determine the efficacy of the treatment. The methods disclosed herein can be used to determine the lipid compositions at different time points by obtaining biological samples and analyzing the biological samples at one or more time points. The lipid compositions can be compared to determine the efficacy of a treatment. In some embodiments, where a determination is made that a treatment or therapy is substantially not effective or detrimental to a subject, one or more adjustments can be made. The methods disclosed herein can be used thereafter to determine the efficacy of the one or more adjustments in one or more therapies or treatments.

In a non-limiting example, the methods disclosed herein can be used to monitor the metastasis of cancer. A biological sample may be obtained at one or more time points from one or more parts of a subject's body. In some embodiments, a biological sample can be obtained from one or more bodily fluids. The one or more bodily fluids can be whole blood, blood serum, blood plasma, blood filtrate, urine, saliva, sputum, breast milk, ascites fluid, synovial fluid, amniotic fluid, semen, cerebrospinal fluid, follicular fluid and tears. The methods disclosed herein can be used to determine the lipid compositions at one or more time points in the one or more bodily fluids, wherein substantial changes in the lipid compositions may suggest metastasis of cancer. The lipid compositions can be compared to, for example, a reference level obtained from the subject at one or more different time points. In other embodiments, the reference level can be obtained from a healthy subject.

In a non-limiting example, the methods disclosed herein can be used to determine the efficacy of different disease treatments. For example, the methods disclosed herein can be used to determine the efficacy of different cancer therapies on one or more subjects. The methods disclosed herein can be used to determine lipid compositions by obtaining biological samples and analyzing the biological samples at one or more time points. The lipid compositions can be compared to, for example, a reference level obtained from the subject at one or more different time points. In other embodiments, the reference level can be obtained from a healthy subject. The lipid compositions determined using the methods disclosed herein can be compared to identify which disease treatments were effective, ineffective, or detrimental.

Also disclosed herein are methods for assessing health status in a subject. The method can, in some embodiments, include administering to a subject a stable isotope; obtaining a biological sample from the subject; analyzing the biological sample or a derivative thereof by mass spectrometry; and determining the rate and/or amount of stable isotope incorporation for one or more lipids in the biological sample or the derivative thereof, wherein an altered rate and/or amount of stable isotope incorporation in the one or more lipids as compared to a reference rate and/or amount of stable isotope incorporation is indicative of the health status of the subject. In some embodiments, the health status of the subject comprises the metabolic function of the subject, for example the lipid metabolic function of the subject. The health status of the subject can also comprise the presence or absence of cancer cells in the subject.

As disclosed here in, a derivative of a biological sample includes, but is not limited to, one or more components of the biological sample, a filtrate of the biological sample, a retentate of the filtered biological sample, a replicate or clone of the biological sample, a portion of the biological sample, and the biological sample that has been partially or substantially purified. For example, the biological sample can contain one or more cells and a derivative of the biological sample can be a cell culture derived from the biological sample. As another example, the biological sample can be a blood sample obtained from a patient and a derivative of the biological sample can be the filtrate of the blood sample, retentate of the filtered blood sample, or the serum portion of the blood sample.

The reference rate and/or amount of stable isotope incorporation can be established using a reference sample from a healthy subject. In some embodiments, the reference rate and/or amount of stable isotope incorporation of a lipid is a rate determined in a biological sample or a derivative thereof from a health subject, for example the reference rate can be a predetermined rate and stored in a database. In some embodiments, the reference rate and/or amount of stable isotope incorporation of a lipid is a rate determined in a biological sample or a derivative thereof from a subject free of cancer, for example the reference rate can be a predetermined rate and stored in a database.

The rate and/or amount of stable isotope incorporation for a lipid may correlate with the turnover rate for the lipid and/or the newly synthesized fraction of the lipid. In some embodiments, the rate and/or amount of stable isotope incorporation for a lipid is positively correlated with the turnover rate for the lipid. In some embodiments, the rate and/or amount of stable isotope incorporation for a lipid is positively correlated with the newly synthesized fraction of the lipid. As disclosed herein, turnover rate and/or the newly synthesized fraction of one or more lipids can be associated with the health status of a subject. For example, a subject may have a higher or lower lipid metabolism because of a disease state, and thus the subject may have a higher or lower lipid turnover rate or a higher or lower newly synthesized fraction of one or more lipids as compared to a health subject or a subject that is free of one or more diseases of interest. The rate and/or amount of stable isotope incorporation in lipids as disclosed herein can be used to evaluate the turnover rate and newly synthesized fraction of the lipids.

In some embodiments, the altered rate and/or amount of stable isotope incorporation in one or more lipids in the subject indicates that the subject has cancer. For example, a subject with cancer can have a higher rate and/or amount of stable isotope incorporation of a lipid (e.g., a cancer-associating lipid as disclosed herein) as compared to a healthy subject or a subject free of cancer. In some embodiments, a subject with cancer has a lower rate and/or amount of stable isotope incorporation of a lipid (e.g., a cancer-associating lipid as disclosed herein) as compared to a healthy subject or a subject free of cancer.

The rate and/or amount of stable isotope incorporation can be used, in some embodiments, to determine metabolic function of a subject. In some embodiments, the altered rate and/or amount of stable isotope incorporation in one or more lipids in the subject indicates that the subject has a metabolic disorder. For example, a subject with a metabolic disorder can have a higher rate and/or amount of stable isotope incorporation of one or more lipids as compared to a healthy subject or a subject free of the metabolic disorder. In some embodiments, a subject with a metabolic disorder has a lower rate and/or amount of stable isotope incorporation of one or more lipids as compared to a healthy subject or a subject free of the metabolic disorder. Non-limiting examples of metabolic disorders include acid lipase disease; Barth syndrome; central pontine myelinolysis, metabolic myopathies; and lysosomal storage disorders such as Hurler syndrome, Niemann-Pick disease, Tay-Sachs disease, Gaucher disease, Fabry disease, Krabbe disease. The rate and/or amount of stable isotope incorporation can be used, in some embodiments, to determine the activity of one or more lipid-related metabolic pathways or determine the rate of flux through one or more lipid-related metabolic active pathways. In some embodiments, the rate and/or amount of stable isotope incorporation of one or more lipids can be used for determining the origination of the one or more lipids. For example, the rate and/or amount of stable isotope incorporation of a lipid may be used to determine the fraction of the consumed lipid versus the fraction of the synthesized lipid or a combination thereof.

In some embodiments, the information derived from the methods disclosed herein can be used for the treatment of cancer. For example, a biological sample derived from a subject can be analyzed by mass spectrometry for determining the abundance of one or more lipids in the biological sample. An altered abundance of the one or more lipids in the biological sample, as compared to a reference lipid abundance level, is indicative of a cancer in the subject. If there is an altered abundance of the one or more lipids suggesting a patient has cancer, then various cancer treatment methods can be used to treat the subject.

Examples of anti-cancer agents which can be used in the treatment of cancer include, but are not limited to, chemotherapeutic agents, radiation agents, bone marrow, biological response modifier, agents that act to reduce cellular proliferation, antimetabolite agents, microtubule affecting agents, hormone modulators, antibodies, and anti-angiogenic agents. Administration of cancer treatments may generally be tailored to the specific intended route of administration. Suitable routes of administration may, for example, include oral, rectal, topical transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

In some embodiments, the information derived from the methods disclosed herein can be used for the treatment of a patient in different cancer stages. For example, a biological sample derived from a patient who is undergoing or has undergone cancer treatment can be analyzed by mass spectrometry for determining the abundance of one or more lipids in the biological sample. An altered abundance of the one or more lipids in the biological sample, as compared to a reference lipid abundance level, is indicative of a cancer in the subject. One or more biological samples can be obtained from the subject at two or more time points, and the biological samples or derivatives thereof can be analyzed by mass spectrometry for determining abundance of at least one of the one or more lipids in the biological samples or derivatives thereof. The lipid abundance can then be compared, wherein a change in the abundance of at least one of the one or more lipids is indicative of a change in cancer progression in the subject.

In some embodiments, the information derived from the methods disclosed herein can be used to determine whether a subject's condition has declined, stayed substantially the same, improved and whether a subject is in remission. Accordingly, the information derived from the methods disclosed herein can also be used to determine the efficacy of cancer treatments.

If the cancer treatment that the patient is undergoing or has undergone is not effective as determined by the method disclosed herein, the attending healthcare provider (e.g., a physician) would be knowledgeable and capable of determining when to terminate, halt, or adjust cancer treatment. Similarly, the attending physician would also know to adjust treatment to higher levels if the clinical response were not adequate or effective, unless doing so would result in toxicity or organ dysfunctions. The magnitude of an administrated dose in the management of cancer will vary with the severity of the cancer to be treated and to the route of administration. For example, the severity of the cancer can be evaluated, in part, by standard prognostic evaluation methods. Further, the dose or dose frequency may also vary according to the age, body weight, and response of the individual subject being treated.

EXAMPLES

Having generally described embodiments of the present application, a further understanding can be obtained by reference to certain specific examples which are provided herein for purposes of illustration only, and are not intended to be limiting.

Example 1

NIMS Surface Fabrication

The production of NIMS chips has been described in Woo et al. Nat. Protoc. 3:1341-1349 (2008). Briefly, a silicon wafer is cleaned thoroughly with methanol, followed by anodic etching with 25% hydrofluoric acid (w/v) in ethanol in a custom made Teflon etching chamber using a current of 2.4 A for 15 minutes. Next, chips are coated by adding the perfluorinated initiator liquid bis(heptadecafluoro-1,1,2,2-tetrahydrodecyl)tetramethyl-disiloxane for 20 minutes. Excess initiator is blown off with nitrogen.

Example 2

Lipid Compositions

In this example, samples including cultured cells (cell pellets from F1 and F10 melanoma cell cultures, cell pellets from T4 invasive breast cancer cell culture, and filtered supernatant from F10 melanoma cell culture) and exosomes isolated from F1 and F10 melanoma cell lines were provided. Each sample was analyzed by nanostructure-initiator mass spectrometry (NIMS) for lipid profiling.

The samples were solvent extracted in MeOH and spotted on the NIMS surface, before being subject to laser desorption analysis in an ABI/Sciex 5800 MALDI TOF/TOF mass spectrometer. The results are shown in FIGS. 1-3.

Figure 2:
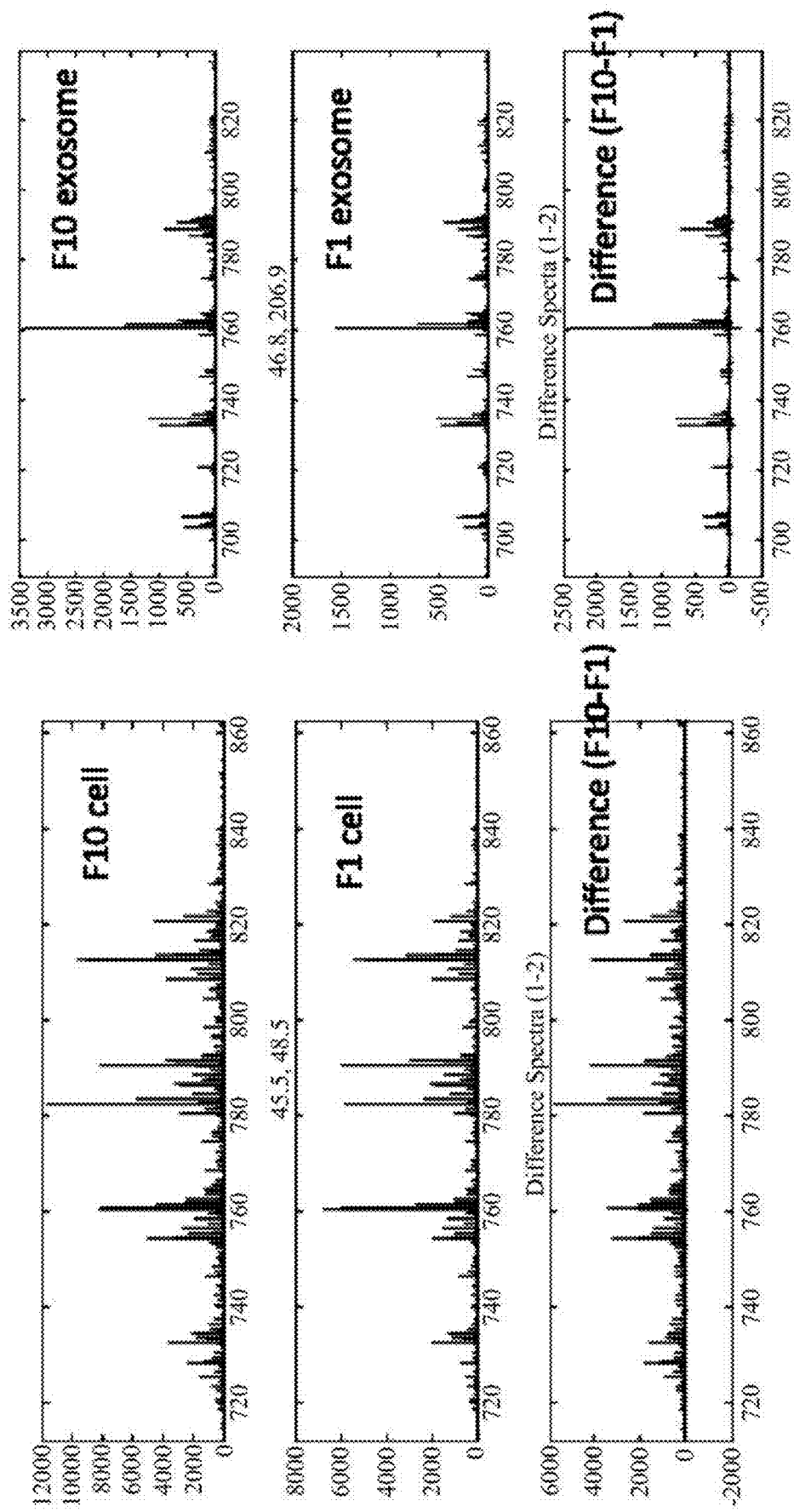
FIG. 2 depicts nanostructure-initiator mass spectrometry (NIMS) spectra showing lipid profiles of F10 and F1 exosomes from F10 and F1 melanoma cell lines and F10 and F1 melanoma cells.

FIG. 1 depicts the NIMS spectra showing lipid profiles of the F10 exosomes derived from F10 melanoma cell culture, as well as the comparison between the lipid profile of F10 exosomes and that of the F10 melanoma cells or the T4 breast cancer cells. FIG. 2 depicts the NIMS spectra showing lipid profiles of exosomes derived from F10 and F1 melanoma cell culture and lipid profile of the F10 and F1 melanoma cell culture. The lipids of exosomes, cells of origin and supernatant were compared and compositional similarity between F1 and F10 exosomes was seen as well as between F1 and F10 parent cells. As shown in FIGS. 1 and 3, lipid composition of the exosomes was more similar to the lipid composition of the crude filtrate and that of the cell line from which the exosomes originated than the lipid composition of an unrelated cancer cell line. These results suggest that crude filtrates of a cell culture can provide a direct readout of cellular metabolism.

In addition, since the NIMS lipid profiles for the F10 exosomes and F10 cells are different from the T4 invasive breast cancer cell line profile in FIG. 1. This result indicates that NIMS profiles can be used to differentiate between cells producing the different microparticles, for example cells of different cancer origin.

NIMS lipid profiling was conducted for purified F10 exosomes derived from F10 melanoma cells lines and compared with NIMS lipid profiling for crude F10 filtered supernatant. FIG. 3A depicts a NIMS lipid profile of the lipid compositions detected. This suggests that NIMS profiles of exosomes and crude filtrates have similar spectra. This may enable a much more high-throughput sample preparation of lipid particles to be used in the methods disclosed herein.

Figure 3B:
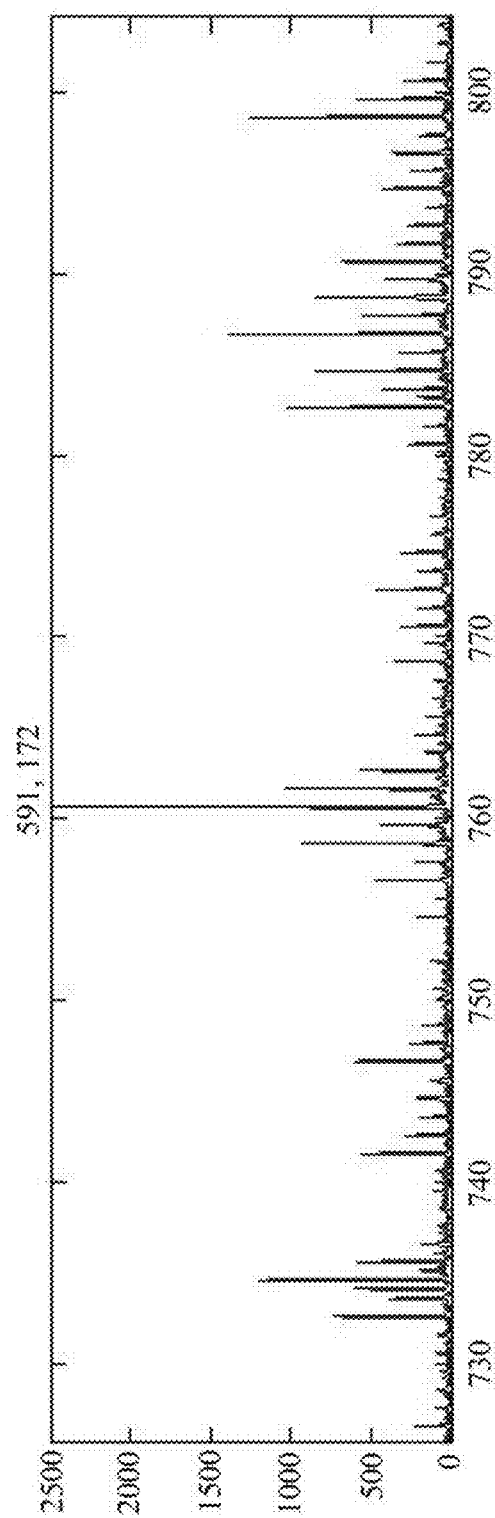
FIG. 3B depicts nanostructure-initiator mass spectrometry (NIMS) spectra showing lipid profile of a breast tumor extract.

NIMS was used to provide a rapid profile of small molecule components of these particles and in particular, this analysis provided a lipid profile. It was found that the ion detected at about m/z 760 ion (referred to as "m/z 760 ion" herein) is abundant in both melanoma and breast cancer cell lines and microparticles. This abundant m/z 760 ion was also found to be abundant in breast tumor extract. FIG. 3B depicts a NIMS profile of breast tumor extract showing abundance of microparticle lipids at about m/z 760. The m/z 760 ion, which is abundant in all of these cancer cell lines and particles, is also abundant in a tumor as shown in FIG. 1. These results indicate that this m/z 760 ion can be used as a diagnostic molecule for highly invasive cancer cells. This m/z 760 ion compound is likely a monounsaturated or saturated lipid that is associated with invasive cancer subtypes.

As shown in FIGS. 1-3, these microparticles may provide a link to the cells that originated the microparticles. Thus, analyzing these microparticles may provide for a non-invasive assay. This may include, for example, an embodiment of the methods disclosed herein where the microparticles are isolated from blood and assayed to provide diagnostic information from the patient.

Samples including F1 melanoma cell culture (F1), F10 melanoma cell culture (F10) and non-metastatic melanoma cell cultures (melan-a), supernatant from each of these three cell cultures, exosomes isolated from each of these three cell cultures, and exosomes isolated from Dulbecco's modified Eagle's medium (DMEM) are provided. And the sample were extracted using a chloroform-based Bligh Dyer lipid extraction and were analyzed using liquid chromatography/mass spectrometry (LC/MS) on a Waters-HILIC column and reverse-phase C18 column on an Agilent 6520. F1 was a low metastatic cell line, F10 was a high metastatic cell line, melan-a was non-metastatic cell line, and DMEM-contained cell culture serum.

FIG. 4 depicts scatterplots of the abundance of ions in each lipid extract for each type of exosome. The results shown in FIG. 4 demonstrate the differences between exosomes from different cancer cell lines and varying with metastatic potential (through n=1). Ion intensities between samples run on LC/MS HILIC were compared for a filtered list of m/z values, with ions detected via LC-QTOF mass spectrometry. The scatterplots showed that non-metastatic exosomes were most different from F1 or F10 exosomes, while F1 and F10 exosomes were more similar to each other than non-metastatic or DMEM exosomes.

Example 3

Lipid Abundance

Figure 5:
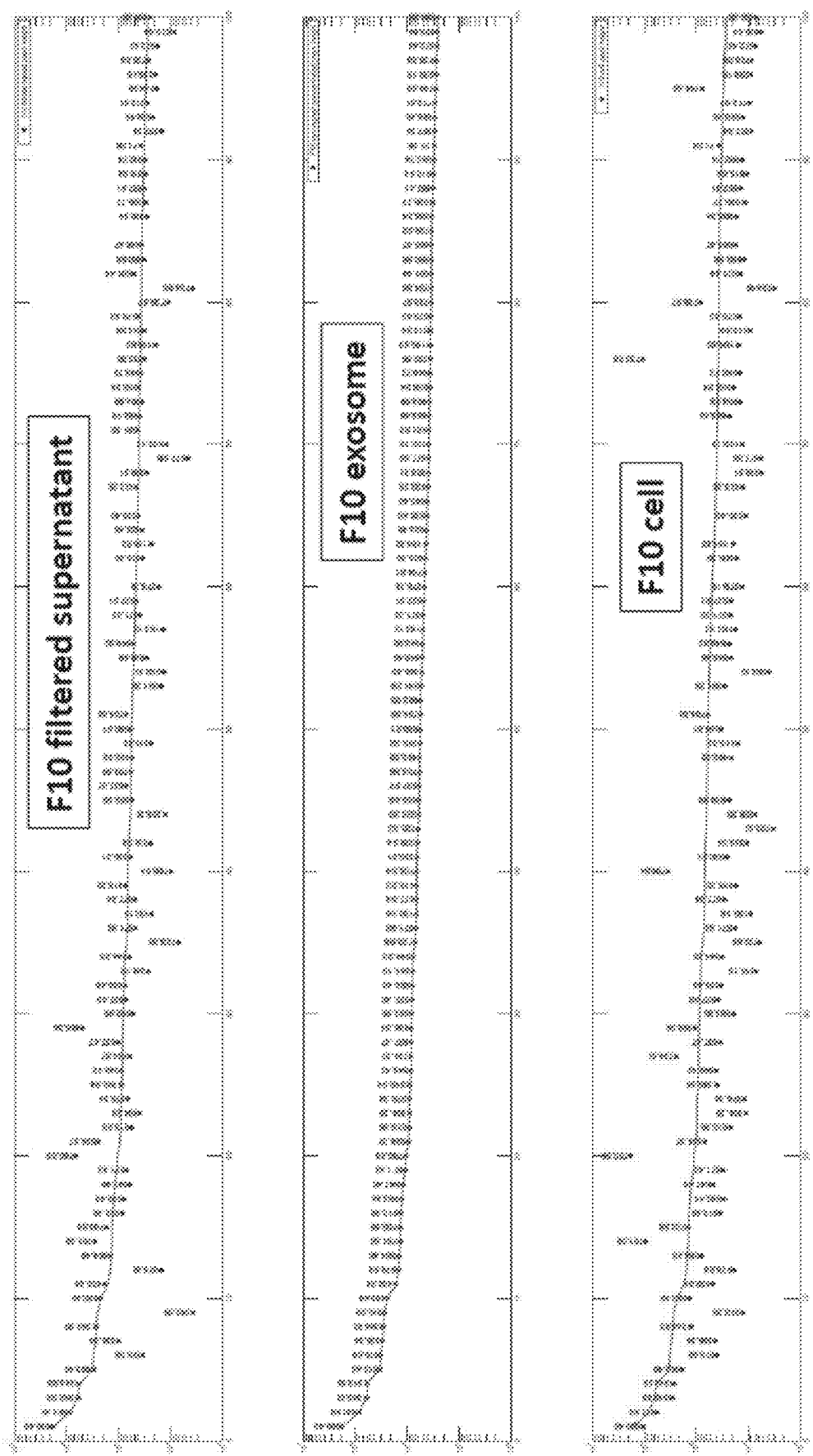
FIG. 5 depicts a graph of a subset of cellular lipids incorporated into exosomes, with the top 100 most abundant F10 exosome lipids ranked by abundance. Comparative abundance in F10 filtered supernatant and F10 cell lipids ranked by abundance is also shown.

Abundance of various cellular lipids in F10 filtered supernatant, F10 exosome and F10 cell were determined using LC-MS. FIG. 5 depicts a graph of intensity values for a subset of cellular lipids incorporated into a F10 filtered supernatant, F10 exosome and F10 cell, with the top 100 most abundant F10 lipids ranked by most abundant m/z values. The values were shown in rank order with the highest to lowest ion intensity. TABLES 1 and 2 show lipids found to be abundant in exosomes isolated from highly metastatic F10 melanoma cells using LC/MS analysis, (SM=sphingomyelin, PS=phosphoserine, PG=phosphatidylglycerol, LysoPE=lysophosphoethanolamine, PE=phosphoethanolamine, LysoPC=lysophosphocholine, and PC=phosphocholine). The peak height of the detected m/z and putative lipid ID, based on accurate mass m/z detected with HMDB and LipidMaps database, is provided. As shown in TABLES 1 and 2, a number of SMs were observed in very high abundance. Most high abundance diacyl lipids were monounsaturated or saturated lipids, whereas polyunsaturated lipids were in much less abundance. TABLE 1 shows that glucosylceramides sphingomyelins, and specific PCs and PEs tend to be upregulated in cancer.

TABLE 1

Abundant Exosome Lipids Detected in F10 Exosomes Using LC/MS

| Detected m/z | Putative Lipid ID | F10 | F1 | melan-a |
| --- | --- | --- | --- | --- |
| 788.616 | PC(34:1) | 1675118 | 1163993 | 247811 |
| 734.569 | PC(32:1) | 421628 | 286441 | 26009 |
| 732.554 | PC(32:0) | 404093 | 256034 | 221739 |
| 703.575 | SM(d34:1) | 380499 | 248859 | 130631 |
| 758.569 | PC(36:2) | 344330 | 275458 | 43132 |
| 758.600 | PC(36:1) | 296162 | 252738 | 54823 |
| 760.585 | PC(30:0) | 272196 | 160335 | 29774 |
| 746.569 | PE(36:2) | 197947 | 125899 | 14283 |
| 746.606 | PC(36:4) | 176227 | 130706 | 37201 |
| 706.538 | PC(34:2) | 170255 | 124595 | 28222 |
| 782.569 | PC(34:2) | 168112 | 125498 | 27959 |
| 808.585 | PC(P-34:0) | 156693 | 143281 | 32495 |
| 724.528 | PE(P-34:1) | 136210 | 103709 | 18276 |
| 496.340 | LysoPC(16:0) | 132139 | 93453 | 7551 |
| 701.559 | SM(d42:2) | 130201 | 95316 | 41922 |

TABLE 1-continued

Abundant Exosome Lipids Detected in F10 Exosomes Using LC/MS

| Detected m/z | Putative Lipid ID | F10 | F1 | melan-a |
|---|---|---|---|---|
| 790.559 | PS(36:1) | 127751 | 96861 | 51037 |
| 744.554 | PE(34:1) | 123941 | 86736 | 9659 |
| 782.569 | PC(36:4) | 105475 | 80299 | 16936 |
| 813.684 | SM(d34:2) | 95757 | 61383 | 11875 |
| 718.538 | PE(36:1) | 78211 | 56112 | 13239 |
| 700.572 | Glucosylceramide (d18:1/16:0) | 76989 | 47940 | 8395 |
| 716.522 | PE(P-38:5) | 75358 | 50421 | 17031 |
| 786.601 | PC(34:0) | 74591 | 47953 | 142304 |
| 762.601 | PC(36:4) | 70752 | 50407 | 20265 |
| 782.569 | PC(38:5) | 69376 | 48157 | 14936 |
| 774.601 | PE(P-36:4) | 68484 | 51124 | 12408 |
| 750.543 | PE(38:1) | 66527 | 51086 | 17438 |
| 784.666 | Glucosylceramide (d18:1/22:0) | 66484 | 50042 | 0 |
| 810.682 | Glucosylceramide (d18:1/24:1) | 57599 | 44272 | 0 |
| 702.543 | PE(34:2) | 55147 | 30808 | 0 |
| 522.355 | LysoPC(18:1(11Z)) | 37500 | 26232 | 0 |

TABLE 2

Abundant Lipids Detected in F10 Exosomes Using LC/MS

| Mean melan-a | Mean F1 | Mean F10 | Putative Lipid ID | Detected m/z |
|---|---|---|---|---|
| 1,673.01 | 5,887.42 | 5,654.88 | Ceramide(d18:1/24:1(15Z)) | 648.6304 |
| 4,536.47 | 11,212.61 | 7,335.25 | Ceramide (d18:1/16:0) or N-Palmitoylsphingosine | 538.5207 |
| 53,767.16 | 189,953.28 | 129,641.00 | Galactosylceramide (d18:1/16:0) | 722.5574 |
| 4,031.18 | 17,857.65 | 14,257.59 | Galactosylceramide (d18:1/16:0) | 700.5739 |
| 5,076.62 | 4,683.53 | 5,534.95 | Galactosylceramide (d18:1/20:0) | 756.6337 |
| 3,087.68 | 2,878.79 | 3,401.27 | Galactosylceramide (d18:1/20:0) | 778.6181 |
| 6,063.23 | 23,278.42 | 31,739.32 | Galactosylceramide (d18:1/24:1(15Z)) | 810.6781 |
| 4,957.32 | 12,080.75 | 19,621.54 | Galactosylceramide (d18:1/24:1(15Z)) | 832.6667 |
| 6,968.43 | 10,083.52 | 13,941.19 | Glucosylceramide (d18:1/22:0) | 784.6613 |
| 2,736.16 | 6,000.34 | 11,194.60 | Glucosylceramide (d18:1/22:0) | 806.6432 |
| 3,402.34 | 10,041.26 | 12,290.37 | Glucosylceramide (d18:1/24:0) | 812.6909 |
| 1,475.44 | 5,644.05 | 6,176.62 | Glucosylceramide (d18:1/24:0) | 834.6793 |
| 38,375.09 | 92,882.17 | 74,635.67 | LysoPC(16:0) | 496.3414 |
| 37,367.57 | 88,350.92 | 73,861.62 | LysoPC(18:0) | 524.373 |
| 6,747.14 | 30,832.49 | 26,028.72 | LysoPC(18:1) | 522.3571 |
| 19,908.56 | 40,980.87 | 44,915.17 | LysoPC(20:3) | 546.3553 |
| 8,239.84 | 6,778.78 | 7,686.86 | LysoPE(16:0) | 454.294 |
| 4,328.62 | 8,658.97 | 4,666.37 | LysoPE(18:0) | 482.3278 |
| 4,024.55 | 19,573.43 | 23,247.40 | LysoPE(18:1) | 480.3097 |
| 3,447.17 | 9,949.82 | 7,895.72 | PC(28:0) | 678.508 |
| 25,834.82 | 10,278.85 | 14,277.31 | PC(28:1) | 676.4939 |
| 17,424.93 | 6,235.20 | 8,509.48 | PC(28:2) | 674.4662 |
| 45,519.93 | 79,553.52 | 84,758.41 | PC(30:0) | 706.5404 |
| 139,392.74 | 74,138.55 | 85,829.09 | PC(32:0) | 734.5717 |
| 48,049.19 | 154,213.14 | 102,032.77 | PC(32:1) | 732.5562 |
| 3,263.93 | 9,013.12 | 3,814.22 | PC(32:2) | 730.5439 |
| 4,868.67 | 4,363.01 | 10,039.88 | PC(32:3) | 728.5267 |
| 40,042.51 | 10,193.49 | 10,501.04 | PC(34:0) | 762.6029 |
| 203,333.70 | 397,259.77 | 340,812.79 | PC(34:1) | 760.5881 |
| 25,170.27 | 50,304.74 | 30,591.58 | PC(34:2) | 758.5715 |
| 23,328.37 | 13,684.01 | 15,552.88 | PC(34:3) | 756.5589 |
| 8,676.36 | 21,138.53 | 17,862.65 | PC(34:4) | 754.5394 |
| 25,621.09 | 72,824.45 | 50,728.43 | PC(36:1) | 788.6188 |
| 19,425.77 | 79,515.97 | 44,868.52 | PC(36:2) | 786.6026 |
| 11,746.06 | 24,827.40 | 13,537.39 | PC(36:3) | 784.5883 |
| 37,272.44 | 28,778.42 | 18,481.16 | PC(36:4) | 782.5723 |
| 24,223.35 | 28,131.92 | 21,167.20 | PC(38:4) | 810.605 |
| 3,962.68 | 13,770.92 | 8,866.95 | PC(38:5) | 808.5852 |
| 21,346.46 | 18,142.82 | 21,731.06 | PC(38:6) | 806.5714 |
| 11,573.87 | 15,655.04 | 13,651.75 | PC(40:6) | 834.6105 |
| 4,243.95 | 6,146.34 | 5,352.58 | PC(40:7) | 832.5859 |
| 4,817.31 | 7,685.90 | 6,594.18 | PC(o-30:0) | 692.5608 |
| 4,883.03 | 16,797.10 | 9,699.03 | PC(P-32:0) | 718.5761 |
| 14,986.39 | 35,196.84 | 23,263.82 | PC(P-34:0) | 746.6074 |
| 1,114.09 | 5,842.14 | 5,072.47 | PE(32:1) | 690.5083 |
| 17,080.66 | 10,155.50 | 9,742.50 | PE(34:0) | 720.5563 |
| 1,356.65 | 15,682.92 | 11,167.75 | PE(34:2) | 716.5241 |
| 26,631.58 | 55,821.01 | 43,201.34 | PE(36:1) | 746.5716 |
| 9,225.58 | 71,722.42 | 61,997.80 | PE(36:2) | 744.5557 |
| 1,524.46 | 5,842.47 | 4,166.78 | PE(36:3) | 742.5397 |
| 7,074.97 | 9,832.31 | 8,506.31 | PE(38:1) | 774.6024 |
| 4,330.92 | 13,329.89 | 9,574.88 | PE(38:2) | 772.5866 |
| 1,323.31 | 11,442.13 | 5,530.47 | PE(38:3) | 770.5705 |

TABLE 2-continued

Abundant Lipids Detected in F10 Exosomes Using LC/MS

| Mean melan-a | Mean F1 | Mean F10 | Putative Lipid ID | Detected m/z |
|---|---|---|---|---|
| 13,904.78 | 12,424.90 | 10,818.99 | PE(38:4) | 768.554 |
| 2,890.72 | 6,318.88 | 8,876.67 | PE(38:5) | 766.5399 |
| 2,028.90 | 10,591.05 | 6,007.06 | PE(P-32:1) | 674.5134 |
| 3,169.26 | 8,233.34 | 7,327.95 | PE(P-34:0) | 704.555 |
| 16,402.48 | 69,981.13 | 56,558.87 | PE(P-34:1) | 702.5451 |
| 2,962.53 | 12,261.06 | 6,815.19 | PE(P-34:2) | 700.5293 |
| 3,147.72 | 18,330.01 | 17,525.62 | PE(P-36:1) | 730.5768 |
| 6,728.90 | 37,321.00 | 25,378.76 | PE(P-36:2) | 728.5592 |
| 2,988.81 | 21,569.97 | 9,240.49 | PE(P-36:3) | 726.5444 |
| 19,961.70 | 20,818.70 | 17,473.52 | PE(P-36:4) | 724.5292 |
| 756.36 | 2,778.31 | 3,976.04 | PE(P-38:1) | 758.6063 |
| 927.68 | 11,182.97 | 5,503.46 | PE(P-38:3) | 754.5757 |
| 13,901.64 | 22,011.53 | 11,468.71 | PE(P-38:4) | 752.5608 |
| 13,680.71 | 14,580.93 | 11,468.71 | PE(P-38:4) | 752.5595 |
| 24,699.14 | 25,901.71 | 19,197.15 | PE(P-38:5) | 750.5451 |
| 6,763.48 | 8,781.47 | 7,289.75 | PE(P-38:6) | 748.531 |
| 2,733.19 | 2,731.69 | 10,602.02 | PE(P-40:2) | 784.628 |
| 7,476.31 | 4,021.54 | 4,908.23 | PE(P-40:5) | 778.5781 |
| 8,813.74 | 6,181.94 | 5,663.33 | PE(P-40:6) | 776.5621 |
| 4,665.56 | 6,298.33 | 3,841.86 | PE(P-40:7) | 774.5456 |
| 7,321.17 | 8,455.20 | 6,404.14 | PE-Ceramide(d14:1/22:0) | 689.5612 |
| 6,573.36 | 5,947.01 | 4,682.20 | PE-Ceramide(d14:1/22:0) | 711.5457 |
| 4,749.62 | 5,695.28 | 7,926.86 | PG(34:1) | 749.5355 |
| 26,256.47 | 3,654.62 | 4,718.14 | PG(34:1) | 766.5602 |
| 583.83 | 6,012.30 | 6,803.41 | PG(34:2) | 747.5208 |
| 2,639.65 | 5,506.83 | 5,813.64 | PG(34:2) | 764.5472 |
| 1,605.65 | 3,593.27 | 5,223.86 | PG(36:1) | 777.566 |
| 5,047.98 | 2,168.49 | 2,675.40 | PG(36:1) | 794.5945 |
| 1,956.93 | 24,006.69 | 23,052.18 | PG(36:2) | 775.5505 |
| 9,733.99 | 23,486.12 | 22,090.39 | PG(36:2) | 792.5765 |
| 4,045.97 | 8,563.72 | 14,171.82 | PS(34:1) | 762.5297 |
| 10,989.86 | 17,666.32 | 22,750.73 | PS(36:1) | 790.5614 |
| 2,926.78 | 5,673.04 | 6,943.15 | PS(36:2) | 788.5477 |
| 399.47 | 2,022.46 | 2,536.78 | PS(40:5) | 838.5617 |
| 7,693.67 | 2,710.40 | 4,867.83 | PS(40:6) | 836.5452 |
| 8,640.07 | 10,534.01 | 10,318.34 | SM(d16:1/16:0) | 675.5451 |
| 10,312.18 | 16,561.95 | 16,654.61 | SM(d18:0/16:0) | 705.5839 |
| 93,825.06 | 142,617.85 | 109,402.01 | SM(d18:0/16:1(9Z)) | 703.5774 |
| 37,714.93 | 21,791.62 | 34,311.60 | SM(d18:0/18:1(11Z)) | 731.6081 |
| 5,035.43 | 3,841.26 | 6,442.70 | SM(d18:0/24:1(15Z)) | 815.7008 |
| 18,436.94 | 8,566.03 | 17,723.07 | SM(d18:1/18:0) | 732.6077 |
| 9,242.70 | 3,849.40 | 12,922.78 | SM(d18:1/22:0) | 787.6636 |
| 19,762.37 | 32,154.23 | 24,398.72 | SM(d18:1/24:1(15Z)) | 813.6856 |
| 6,456.50 | 9,618.21 | 8,169.44 | SM(d18:1/24:1) | 835.6672 |
| 6,456.50 | 9,618.21 | 8,169.44 | SM(d18:1/24:1) | 835.6659 |
| 19,393.88 | 19,919.88 | 18,420.91 | SM(d18:2/16:0) | 701.5613 |

Figure 6:
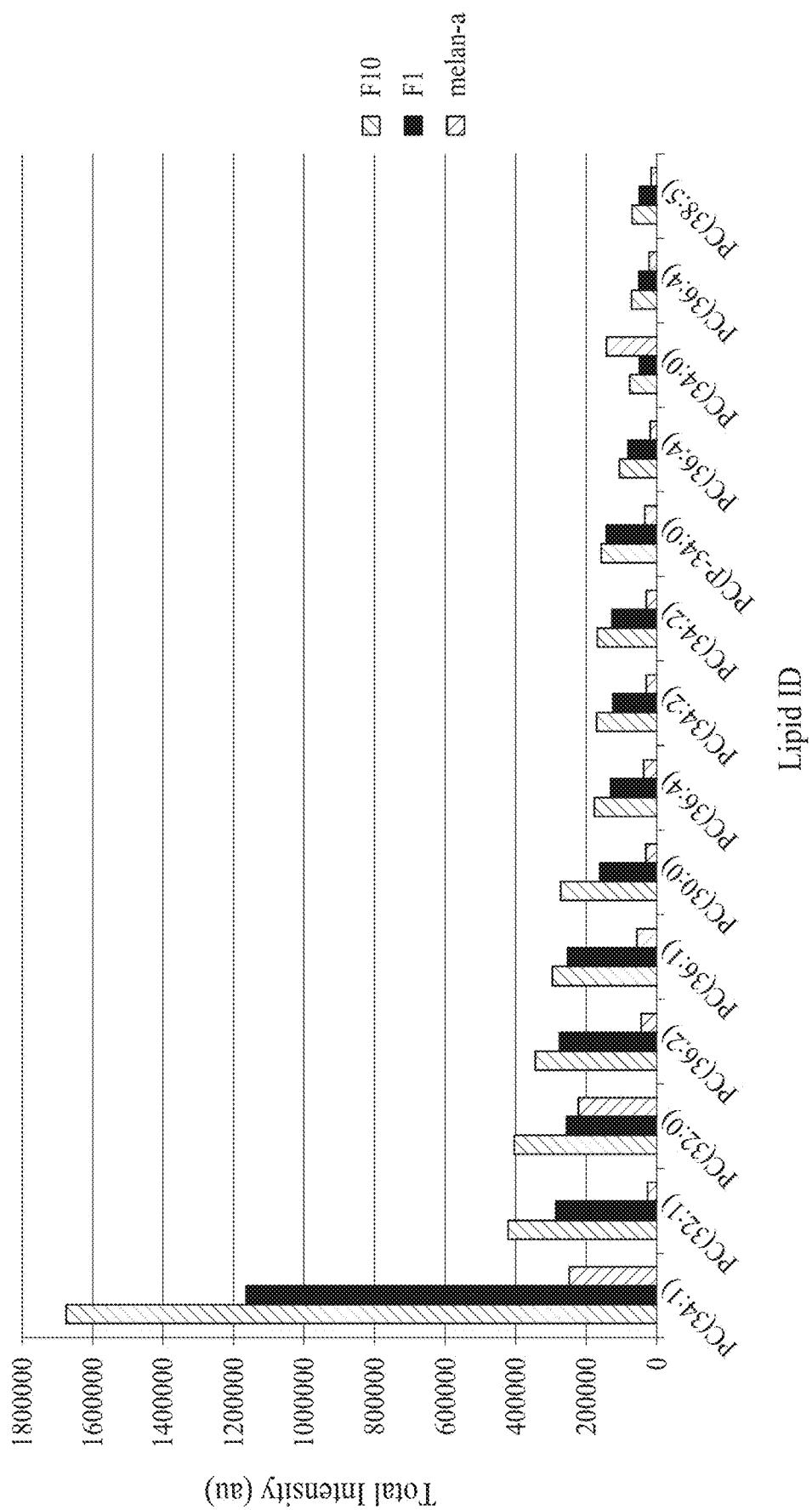
FIG. 6 is a bar graph showing the relative abundance of exosome phosphatidylcholine (PC) lipids in F1, F10 and non-metastatic cells.
Figure 7:
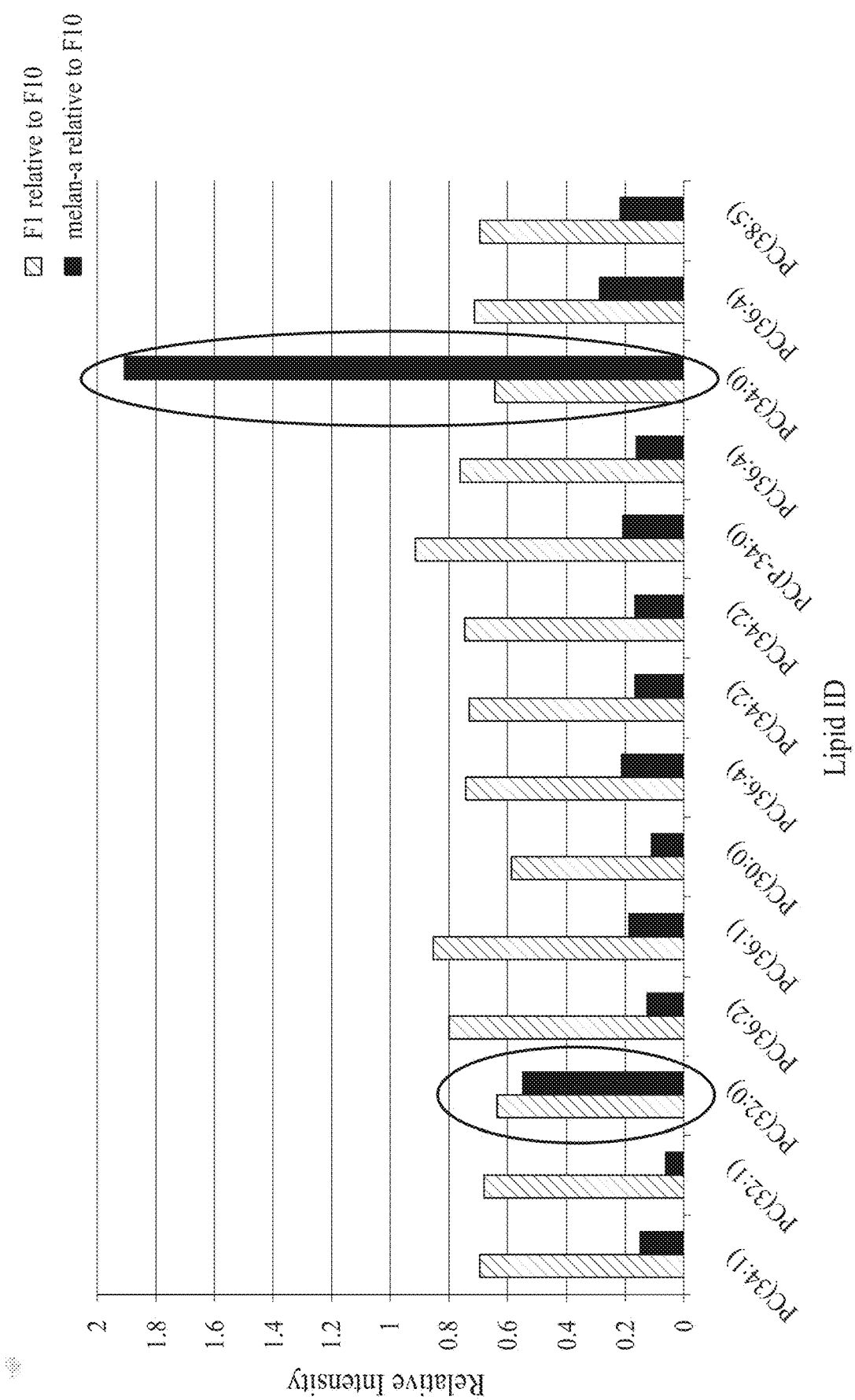
FIG. 7 is a bar graph showing lipid abundance in F1 and non-metastatic cells relative to highly metastatic F10 cells.

A sample of F1, F10 and non-metastatic cells was analyzed to determine the relative intensity of each lipid detected in a sample of exosome phosphatidylcholine (PC) lipids. FIG. 6 depicts a graph showing the relative intensity of each lipid detected in a sample of exosome phosphatidylcholine (PC) lipids in F1, F10 and non-metastatic (melan-a) cells. FIG. 7 depicts a graph showing the PC lipid abundance in F1 and non-metastatic cells in a sample normalized to the specific m/z intensity detected in the highly metastatic F10 cells. This suggested two lipids with cell-specific abundance: PC(34:0) was higher in non-metastatic exosomes than F10 exosomes or F1 exosomes and PC(32:0) was not higher in F1 (low metastatic) versus non-metastatic cells.

A sample of F1, F10 and non-metastatic cells was also analyzed to determine the relative abundance of exosome glucosylceramide and sphingomyelin (SM) lipids. FIG. 8A depicts the relative abundance of putatively identified glucosylceramide detected in a sample normalized to the specific m/z intensity detected in the F10 cell sample. FIG. 8B depicts the relative abundance of putatively identified SM lipids detected in a sample normalized to the specific m/z intensity detected in the F10 cell sample. Glucosylceramide and SM lipids were minimally or not detected at all in non-metastatic cells but highly upregulated in metastatic cancer.

Example 4

Isotopic Labeling of Lipids

Figure 9:
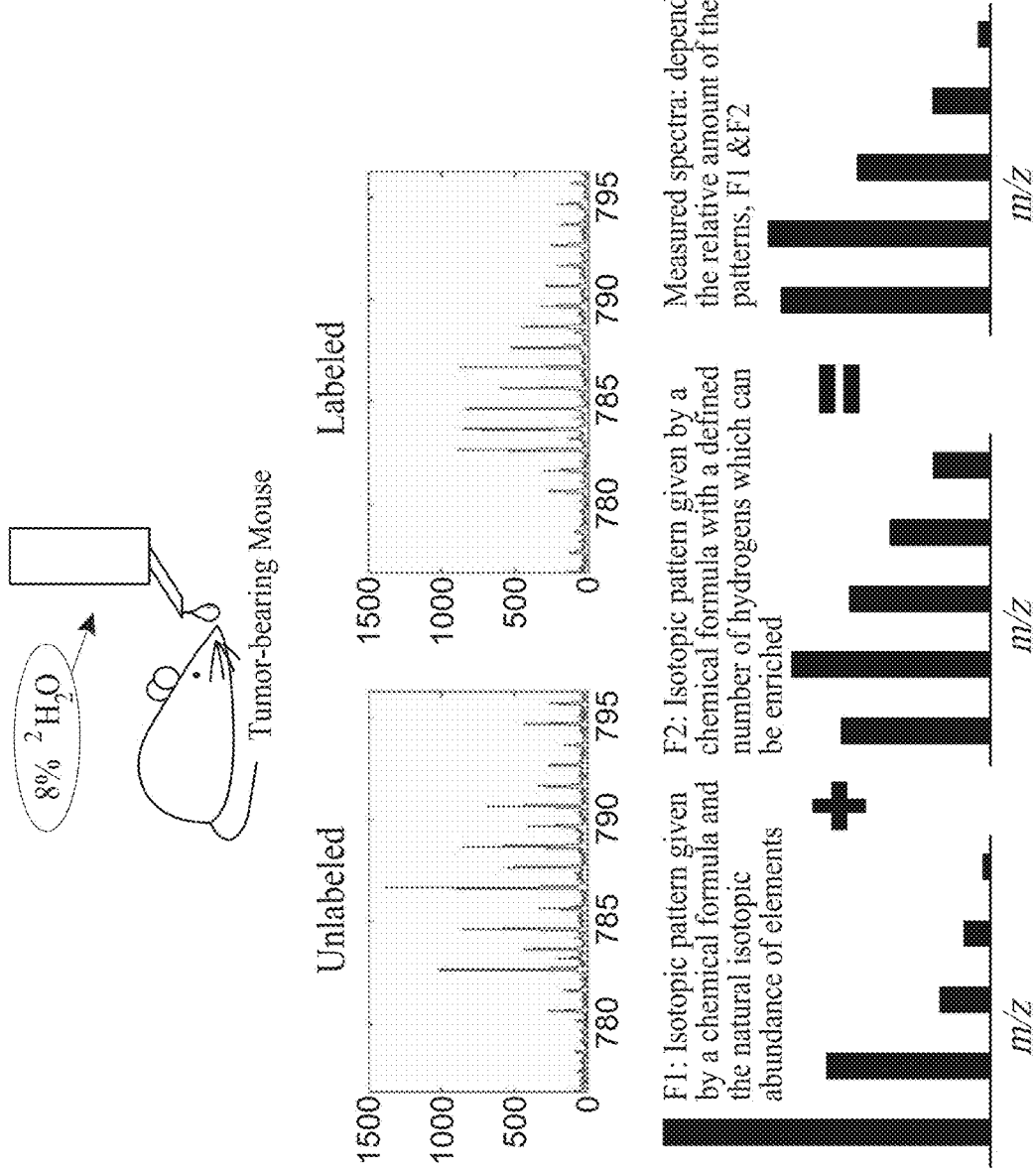
FIG. 9 depicts a schematic illustration of a non-limiting example of stable isotopic labeling with deuterium and subsequent analysis by mass spectrometry.
Figure 9:
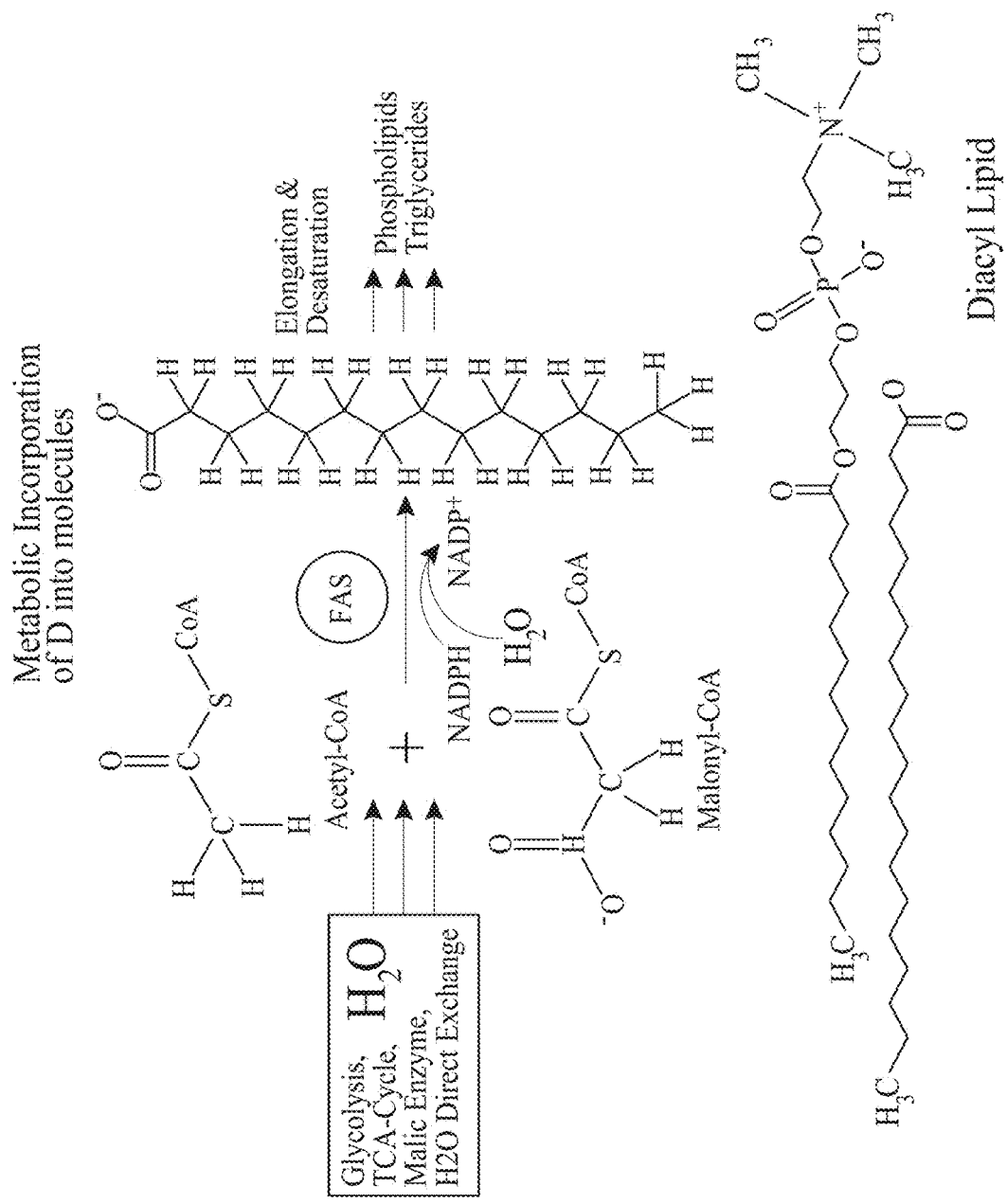

FIG. 9 depicts a schematic illustration of a non-limiting example of stable isotopic labeling of synthesized lipids with deuterium and subsequent analysis by mass spectrometry. FIG. 9 is derived from Louie et al. *Nature Sci. Rep.* 2013, 3, 2045-2322, the content of Louie et al. is hereby incorporated by reference. Solid mammary tumors were obtained by transplanting Trp53-null mammary epithelium fragments (Balb/c background) into the cleared fat pad of F1 backcross female mice generated by the female interspecific F1 hybrid mice between BALB/c and SPRET/EiJ crossing with BALB/c male mice. $^2H_2O$ was administered by injecting a 30 mL/kg intraperitoneal bolus dose of sterile 99.9% $^2H_2O$+0.1% NaCl, followed by free access to drinking water (8% $^2H_2O$) and standard mouse chow Animals were euthanized 5 days after $^2H_2O$ administration, then mammary tumor and serum collected and immediately flash-frozen on dry ice and stored at −80° C. As an unlabeled control, tumor and serum were also collected from a mouse never given $^2H_2O$. Animal treatment and care was performed in accordance with animal protocols approved by the Animal Welfare and Research Committee at Lawrence Berkeley National Laboratory (AUP 9111 & 27010).

Figure 10A:
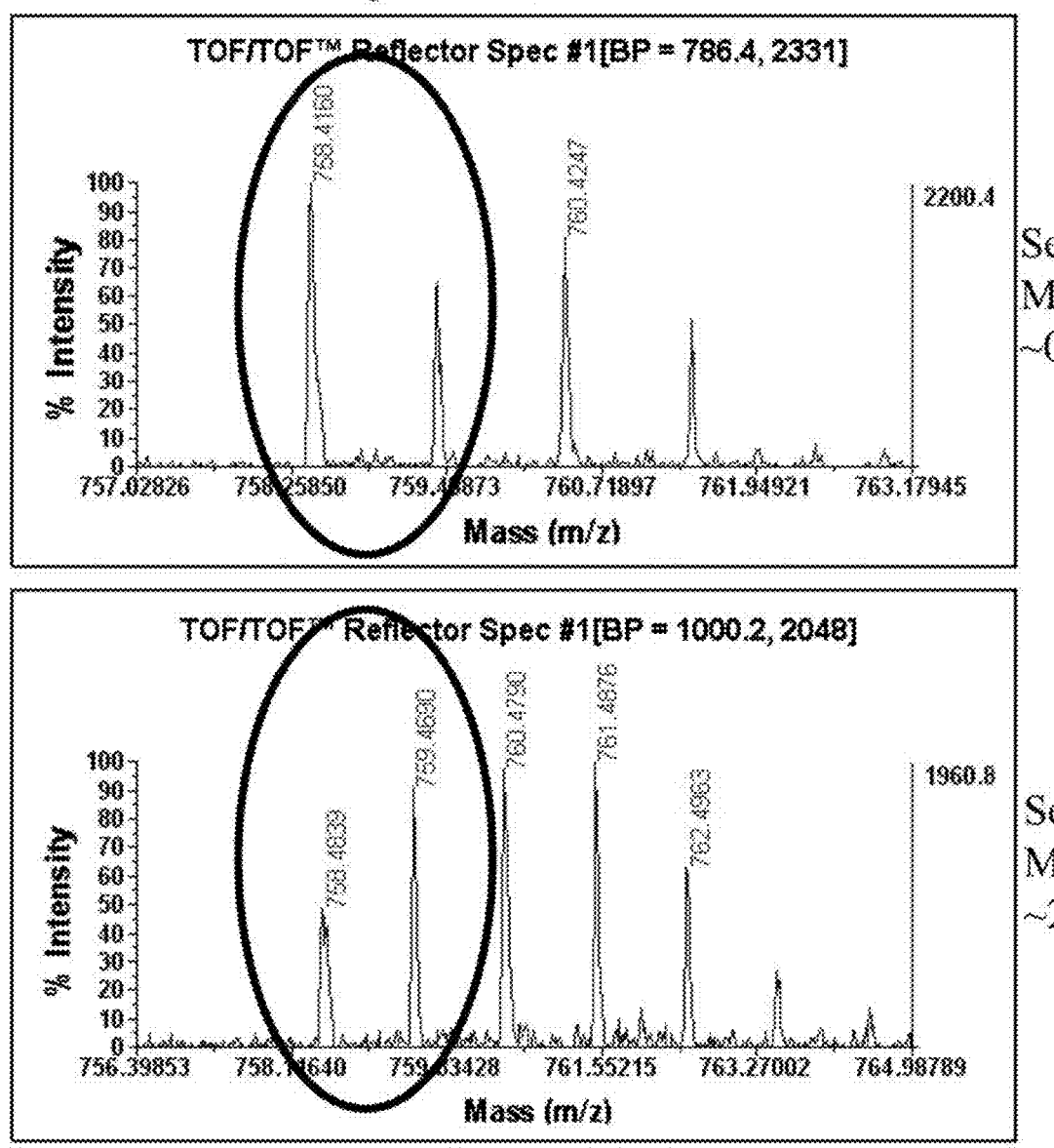
FIG. 10A depicts exemplary mass spectra of a microparticle lipid in serum—turnover of lipid phosphatidylcholine (PC) (36:02) detected by mass spectrometry at m/z 758.6.
Figure 10B:
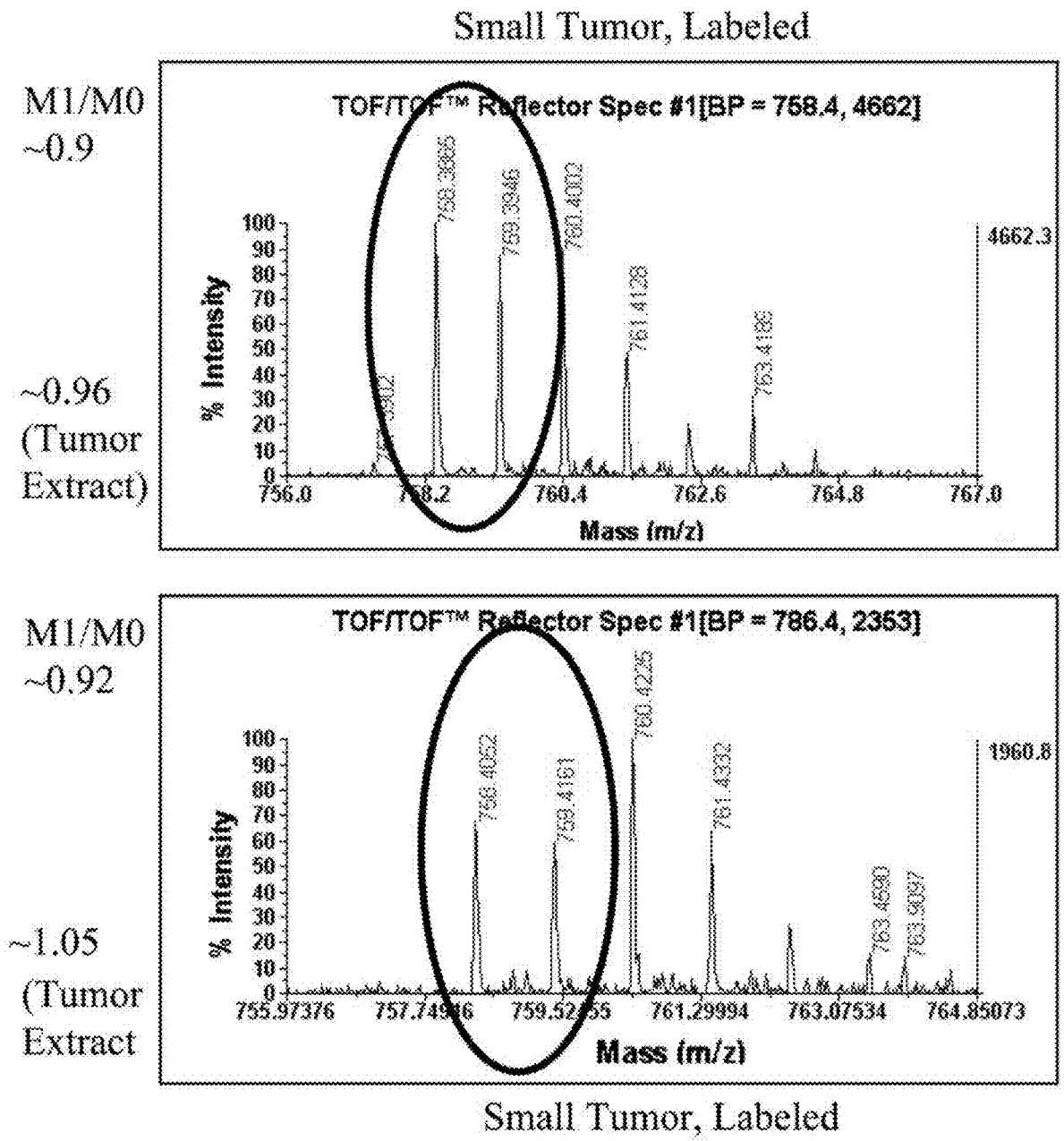
FIG. 10B depicts exemplary mass spectra of a microparticle lipid in a non-specific extract from a tumor showing turnover of a lipid phosphatidylcholine PC(36:02) that was detected by mass spectrometry at m/z 758.6.
Figure 111:
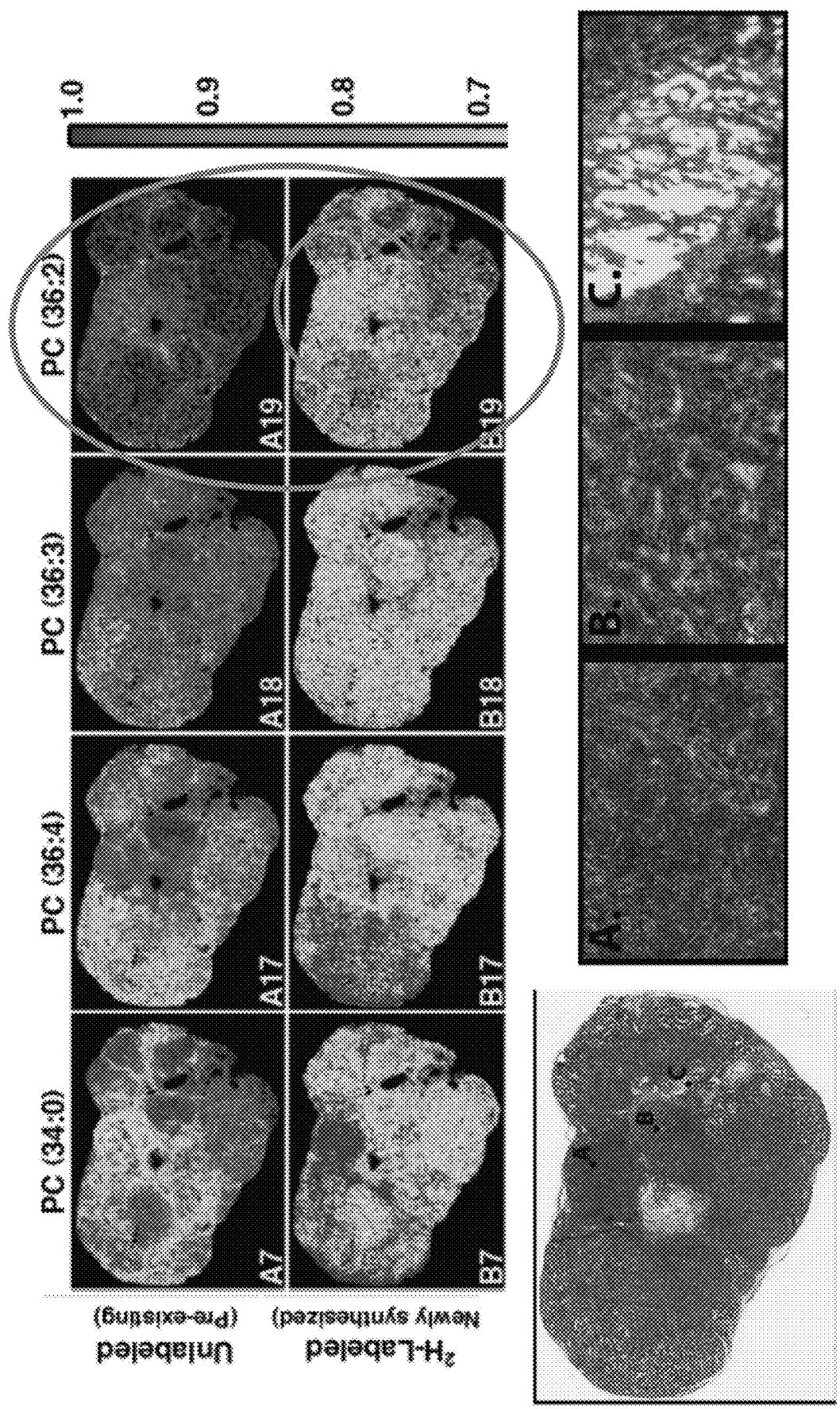
Figure 12:
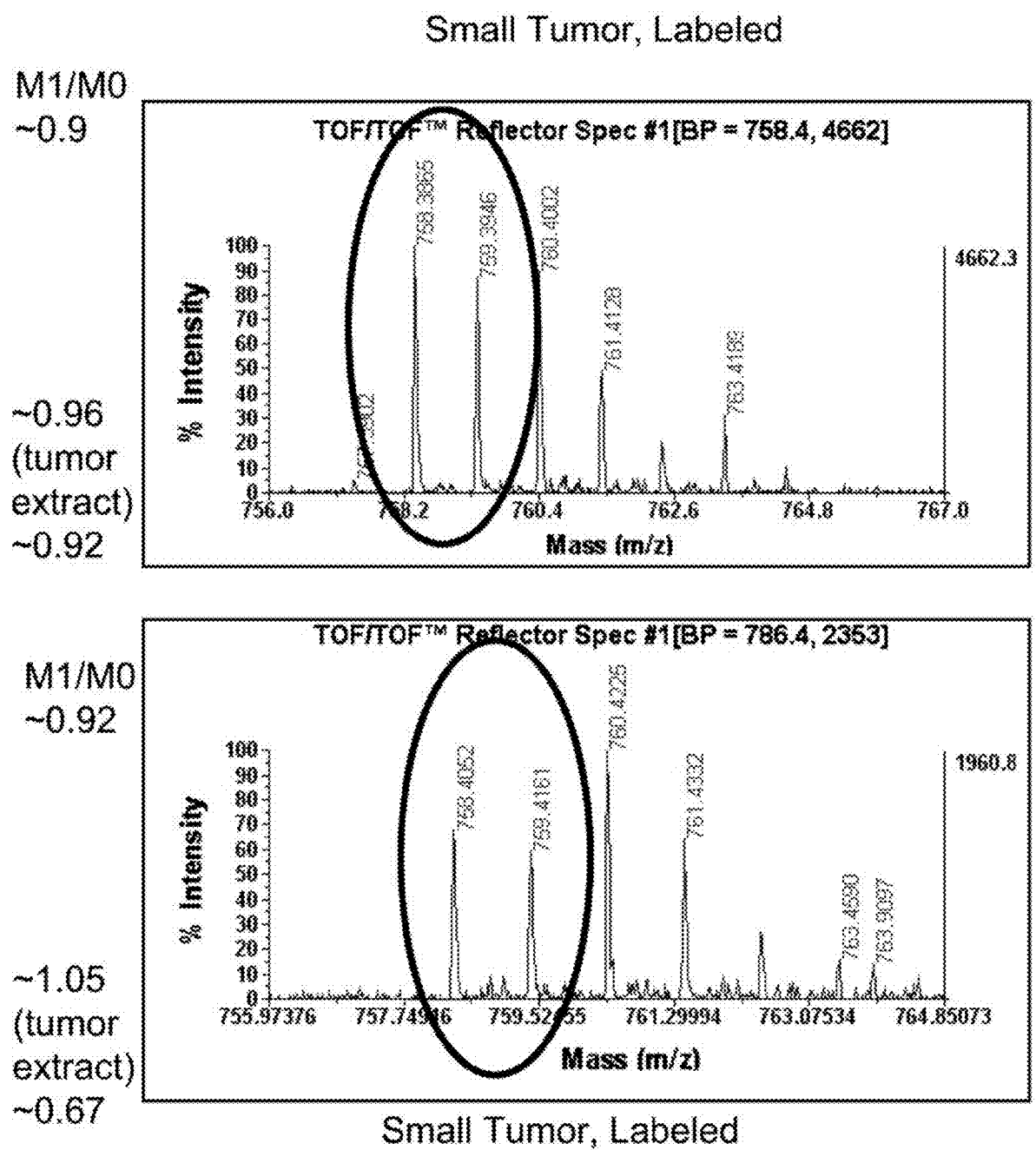
FIG. 12 depicts exemplary mass spectra and the isotopic enrichment of microparticle lipids in serum showing turnover of a lipid phosphatidylcholine PC(36:02) that was detected by mass spectrometry at m/z 758.6.
Figure 12:
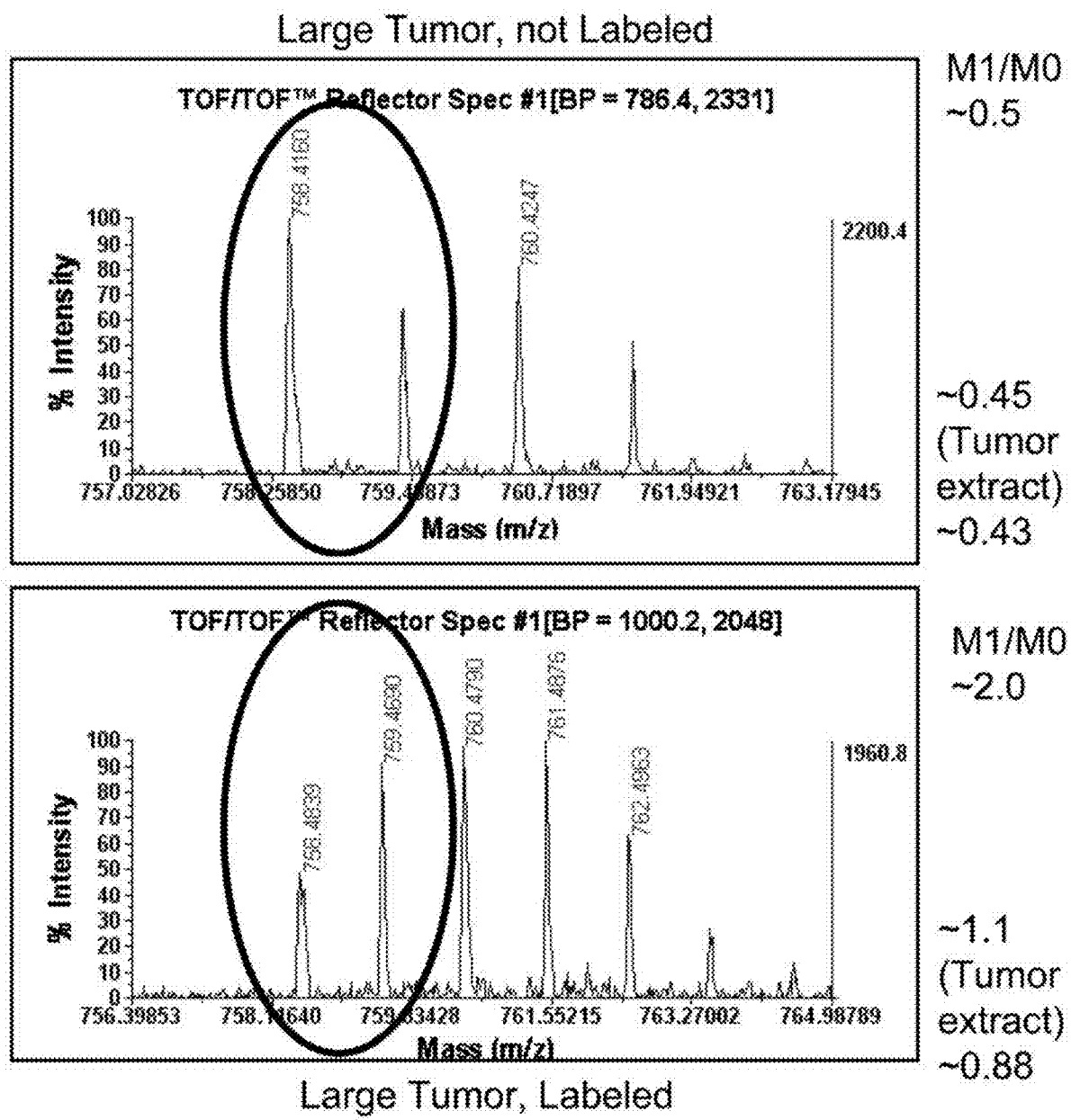

Tumor and serum samples from deuterium and non-deuterium administered mice, as described above, were extracted using a chloroform-based Bligh Dyer lipid extraction. Samples were then spotted on a NIMS chip in MeOH and mass spectra were obtained using an ABI/Sciex 5800 MALDI TOF/TOF mass spectrometer. FIG. 10A shows four exemplary mass spectra of a microparticle lipid in serum showing turnover of putatively identified lipid phosphatidylcholine (PC) (36:02) detected at m/z 758.6, the fifth most abundant F10 exosome lipid, with M0 detected at m/z 758.6 for each sample. The relative ratio between the M1 (m/z 759.6) and M0 (m/z 758.6) isotopes were roughly calculated for a serum sample, FIG. 10A, from each animal and a corresponding non-specific extract from a tumor, FIG. 10B. In FIG. 10A, the larger, fastest growing tumor had the highest rate of new synthesis of this lipid, as detected in serum extract, circled. In FIG. 10B, however, this rate did not correspond with the rate the lipid was synthesized in a non-specific direct extract from the tumor itself (e.g. biopsy, representative of only part of a tumor), but to a specific part of the tumor that was identified as high grade. The direct extract tumor spectra did not correspond with tumor size in the same manner as the serum microparticles. FIG. 11 shows digital images of heterogeneous spatial distribution of lipids for labeled vs. unlabeled populations. The highly synthesized lipid detected in the tumor was being made primarily only in a high grade tumor region, not throughout the entire tumor. FIG. 12 shows four exemplary mass spectra and the isotopic enrichment of microparticle lipids in serum showing turnover of lipid phosphatidylcholine (PC) (36:02) detected at m/z 758.6. The isotopic enrichment of lipids found in serum can be mapped back to the tissue where the lipid was synthesized or modified. This case shows that the labeling of serum lipids is associated with the metabolism of a tumor in the animal. In contrast to PC(36:02) in the tumor extract, rate of synthesis of a different tumor lipid (bottom number), as seen in the tumor extract, corresponded well with tumor size and growth rate.

Example 5

Determining Compositional Similarity Using NIMS Lipid Profiling

The methods disclosed herein can be used in NIMS profiling of lipids of exosomes derived from various cancer cells. For example, lipid compositions of prostate cancer cells, including cultured cells (cell pellets from prostate cell lines and filtered supernatant) and exosomes isolated from prostate cancer cells, respectively, can be analyzed by nano-structure-initiator mass spectrometry (NIMS) lipid profiling. The samples can be solvent extracted in MeOH and placed on the NIMS surface, before being subject to laser desorption analysis in a ABI/Sciex 5800 MALDI TOF/TOF mass spectrometer. NIMS lipid profiling of, for example, the exosomes, cells of origin and supernatant from prostate cancer cells can be compared to determine compositional similarity and differentiate between cells producing different microparticles.

Example 6

Cancer Treatment

A patient suspect of cancer (e.g., breast cancer or melanoma) is identified. A crude blood filtrate obtained from the patient is analyzed by mass spectrometry (e.g., NIMS) for evaluating the lipid composition of the filtrate. The abundance of one or more cancer-related lipids disclosed herein is determined and compared to a reference level for the lipid in a healthy individual. If the lipid abundance level in the blood filtrate is altered as compared to the reference level (e.g., with statistical significance), it indicates that that the patient has cancer. The patient can then be subject to conventional cancer therapy, e.g., chemotherapy, to treat cancer.

The above description discloses several methods and materials of the present invention. This invention is susceptible to modifications that will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. All references cited herein are incorporated by reference in their entirety and are hereby made a part of this specification.

The foregoing description and examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof. Although the present application has been described in detail above, it will be understood by one of ordinary skill in the art that various modifications can be made without departing from the spirit of the invention.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein including, but not limited to, published and unpublished patent applications, patents, text books, literature references, and the like, to the extent that they are not already, are hereby incorporated by reference in their entirety. To the extent that one or more of the incorporated literature and similar materials differ from or contradict the disclosure contained in the specification, including but not limited to defined terms, term usage, described techniques, or the like, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method for identifying one or more diseased cells in a subject, comprising:
   (a) providing a cell culture derived from a biological sample of a subject;
   (b) analyzing a crude extract of the cell culture by mass spectrometry on a nanostructure-initiator mass spectrometry (NIMS) chip having a perfluorinated coat;
   (c) determining the abundance of one or more lipids in the cell culture, wherein an altered abundance of the one or more lipids in the cell culture, as compared to a reference level, identifies a subject as having one or more diseased cells, wherein the one or more diseased cells comprise cancer cells, wherein at least one of the one or more lipids comprises a lipid detected by mass spectrometry, wherein the at least one of the one or more lipids comprises PC(30:0), PE(36:2), PC(P-34:0), PE(P-34:1), PS(36:1), PE(34:1), PE(36:1), Glucosylceramide (d18:1/16:0), PC(34:0), PE(P-36: 4), PE(38: 1), Glucosylceramide (d18: 1/22:0), Glucosylceramide (d18:1/24:1), PE(34:2), or a combination thereof; and
   (d) treating the subject identified as having one or more diseased cells with one or more anti-cancer agents.

2. The method of claim 1, wherein the reference level is established using a reference sample from a healthy subject.

3. The method of claim 1, wherein the cell culture comprises one or more lipid-containing microparticles.

4. The method of claim 3, wherein the one or more lipid-containing microparticles are exosomes, cell membrane fragments, cellular and intracellular organelle fragments, lipid bilayers, or a combination thereof.

5. The method of claim 1, wherein determining the abundance of one or more lipids in the cell culture comprises determining the lipid composition of the cell culture.

6. The method of claim 1, wherein at least one of the one or more lipids is a monounsaturated lipid or a saturated lipid.

7. The method of claim 1, wherein at least one of the one or more lipids comprises a lipid detected by mass spectrometry at about m/z 648.6304, at about m/z 538.5207, at about m/z 722.5574, at about m/z 700.5739, at about m/z 756.6337, at about m/z 778.6181, at about m/z 810.6781, at about m/z 832.6667, at about m/z 784.6613, at about m/z 806.6432, at about m/z 812.6909, at about m/z 834.679337, at about m/z 496.3414, at about m/z 524.373, at about m/z 522.3571, at about m/z 546.3553, at about m/z 454.294, at about m/z 482.3278, at about m/z 480.3097, at about m/z 678.508, at about m/z 676.4939, at about m/z 674.4662, at about m/z 706.5404, at about m/z 734.5717, at about m/z 732.5562, at about m/z 730.5439, at about m/z 728.5267, at about m/z 762.6029, at about m/z 760.5881, at about m/z 758.5715, at about m/z 756.5589, at about m/z 754.5394, at about m/z 788.6188, at about m/z 786.6026, at about m/z 784.5883, at about m/z 782.5723, at about m/z 810.605, at about m/z 808.5852, at about m/z 806.5714, at about m/z 834.6105, at about m/z 832.5859, at about m/z 692.5608, at about m/z 718.5761, at about m/z 746.6074, at about m/z 690.5083, at about m/z 720.5563, at about m/z 716.5241, at about m/z 746.5716, at about m/z 744.5557, at about m/z 742.5397, at about m/z 774.6024, at about m/z 772.5866, at about m/z 770.5705, at about m/z 768.554, at about m/z 766.5399, at about m/z 674.5134, at about m/z 704.555, at about m/z 702.5451, at about m/z 700.5293, at about m/z 730.5768, at about m/z 728.5592, at about m/z 726.5444, at about m/z 724.5292, at about m/z 758.6063, at about m/z 754.5757, at about m/z 752.5608, at about m/z 752.5595, at about m/z 750.5451, at about m/z 748.531, at about m/z 784.628, at about m/z 778.5781, at about m/z 776.5621, at about m/z 774.5456, at about m/z 689.5612, at about m/z 711.5457, at about m/z 749.5355, at about m/z 766.5602, at about m/z 747.5208, at about m/z 764.5472, at about m/z 777.566, at about m/z 794.5945, at about m/z 775.5505, at about m/z 792.5765, at about m/z 762.5297, at about m/z 790.5614, at about m/z 788.5477, at about m/z 838.5617, at about m/z 836.5452, at about m/z 675.5451, at about m/z 705.5839, at about m/z 703.5774, at about m/z 731.6081, at about m/z 815.7008, at about m/z 732.6077, at about m/z 787.6636, at about m/z 813.6856, at about m/z 835.6672, at about m/z 835.6659, at about m/z 701.5613, or a combination thereof.

8. The method of claim 1, wherein the cell culture comprises exosomes.

9. The method of claim 1, wherein the at least one of the one or more lipids comprises PC(30:0).

10. The method of claim 1, wherein the at least one of the one or more lipids comprises PC(30:0), PE(36:2), PC(P-34:0), PE(P-34:1), PS(36:1), PE(34:1), PE(36: 1), Glucosylceramide (d18: 1/16: 0), PC(34:0), PE(P-36: 4), PE(38: 1), Glucosylceramide (d18:1/22:0), Glucosylceramide (d18:1/24:1), and PE(34:2).

* * * * *